US011839874B2

(12) United States Patent
Toh et al.

(10) Patent No.: US 11,839,874 B2
(45) Date of Patent: Dec. 12, 2023

(54) PLANAR MODULAR MICROFLUIDIC SYSTEM

(71) Applicant: NATIONAL UNIVERSITY OF SINGAPORE, Singapore (SG)

(72) Inventors: Yi-Chin Toh, Singapore (SG); Jun Ye Louis Ong, Singapore (SG); Christopher Tostado, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 367 days.

(21) Appl. No.: 16/758,406

(22) PCT Filed: Oct. 23, 2018

(86) PCT No.: PCT/SG2018/050525
§ 371 (c)(1),
(2) Date: Apr. 23, 2020

(87) PCT Pub. No.: WO2019/083447
PCT Pub. Date: May 2, 2019

(65) Prior Publication Data
US 2020/0246796 A1    Aug. 6, 2020

(30) Foreign Application Priority Data

Oct. 23, 2017   (SG) ............................. 10201708700S

(51) Int. Cl.
*B01L 3/00*         (2006.01)
(52) U.S. Cl.
CPC ... *B01L 3/502715* (2013.01); *B01L 3/502707* (2013.01); *B01L 2200/12* (2013.01);
(Continued)

(58) Field of Classification Search
CPC ......... B01L 3/502715; B01L 3/502707; B01L 2200/12; B01L 2200/14; B01L 2300/041;
(Continued)

(56) References Cited

U.S. PATENT DOCUMENTS 6,319,476 B1 * 11/2001 Victor, Jr. ............... B01L 3/563
422/537
2004/0096359 A1   5/2004 Sarrut et al.
(Continued)

FOREIGN PATENT DOCUMENTS

CN      107108199 A     8/2017
WO   2004/022233 A1    3/2004
(Continued)

*Primary Examiner* — Christine T Mui
(74) *Attorney, Agent, or Firm* — SOROKER AGMON NORDMAN PTE LTD

(57) ABSTRACT

A planar modular microfluidic module, system and method for manufacturing such module is provided. The module includes a base layer, and a fluidic layer configured to be attached to and on top of the base layer, whereby the base layer and said fluidic layer configured to create a single basic module, a jacket configured to cover the base module around its lateral sides, in order to provide sturdiness to the basic module and create a jacket covered module. The jacket includes a physical connector configured to enable lateral connection between adjacent modules, the physical connector positioned on at least one lateral side of the jacket covered module, and a fluidic connection port located within said physical connector and configured to enable fluid flow connection between adjacent modules.

29 Claims, 13 Drawing Sheets

(52) U.S. Cl.
CPC ..... *B01L 2200/14* (2013.01); *B01L 2300/041* (2013.01); *B01L 2300/042* (2013.01); *B01L 2300/06* (2013.01); *B01L 2300/0861* (2013.01); *B01L 2300/12* (2013.01)

(58) Field of Classification Search
CPC ........... B01L 2300/042; B01L 2300/06; B01L 2300/0861; B01L 2300/12
USPC ................................................ 422/502, 500
See application file for complete search history.

(56) References Cited

U.S. PATENT DOCUMENTS

| | | |
|---|---|---|
| 2004/0164010 A1 | 8/2004 | Bayer et al. |
| 2010/0247380 A1 | 9/2010 | Lohf et al. |
| 2010/0322826 A1 | 12/2010 | Locascio et al. |
| 2012/0180884 A1* | 7/2012 | Brunello ........... B01L 3/502715 422/503 |
| 2016/0339429 A1 | 11/2016 | Mershin et al. |

FOREIGN PATENT DOCUMENTS

| | | |
|---|---|---|
| WO | 2007/131925 A1 | 11/2007 |
| WO | 2011/066219 A1 | 6/2011 |

\* cited by examiner

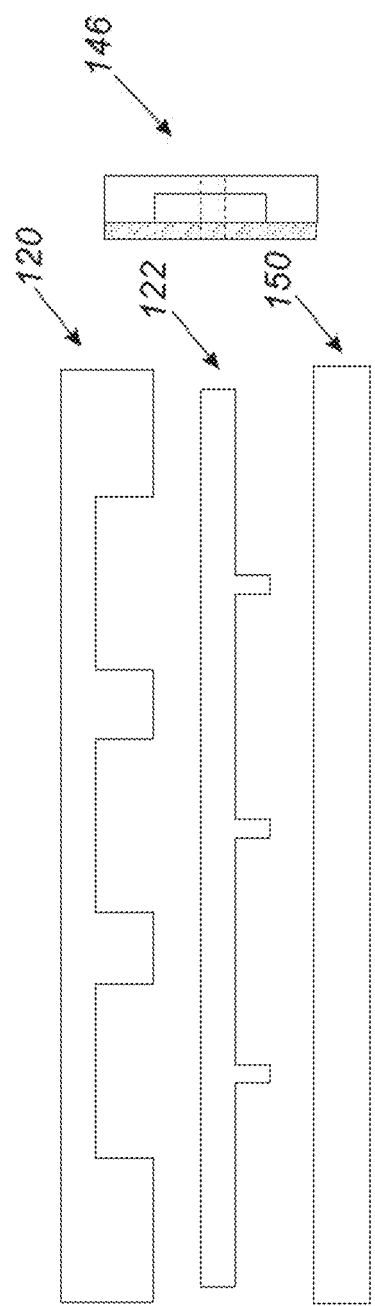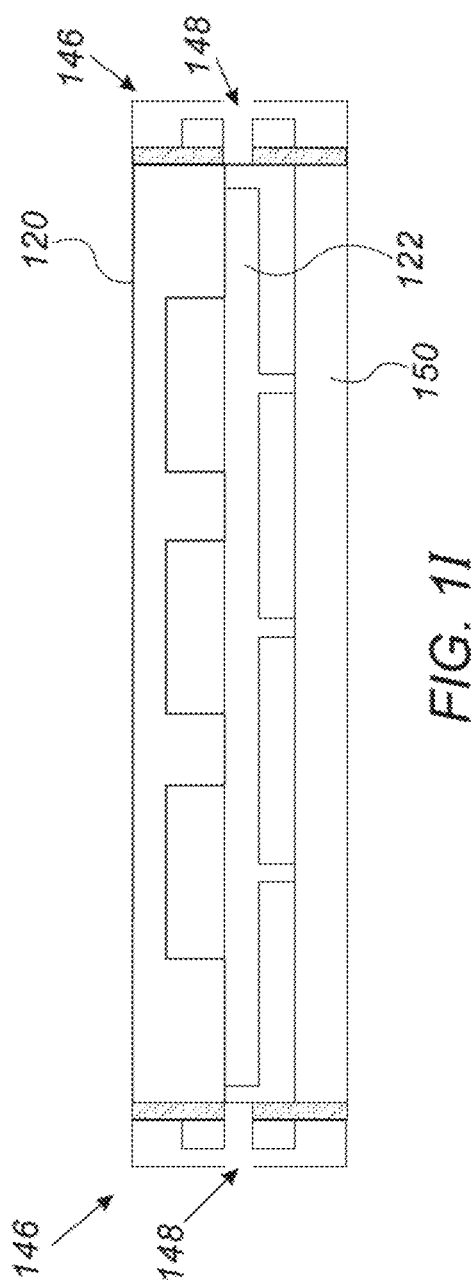

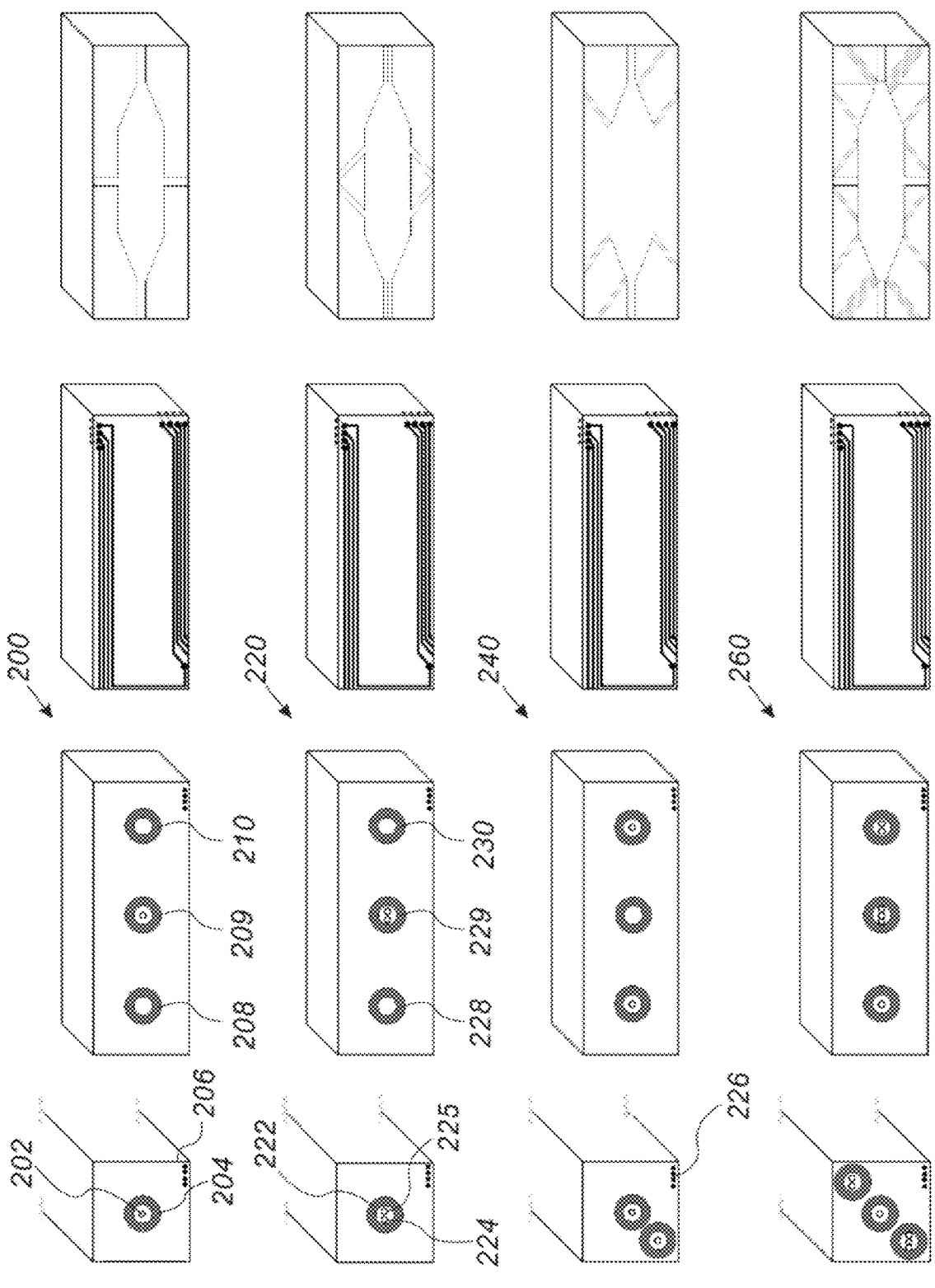

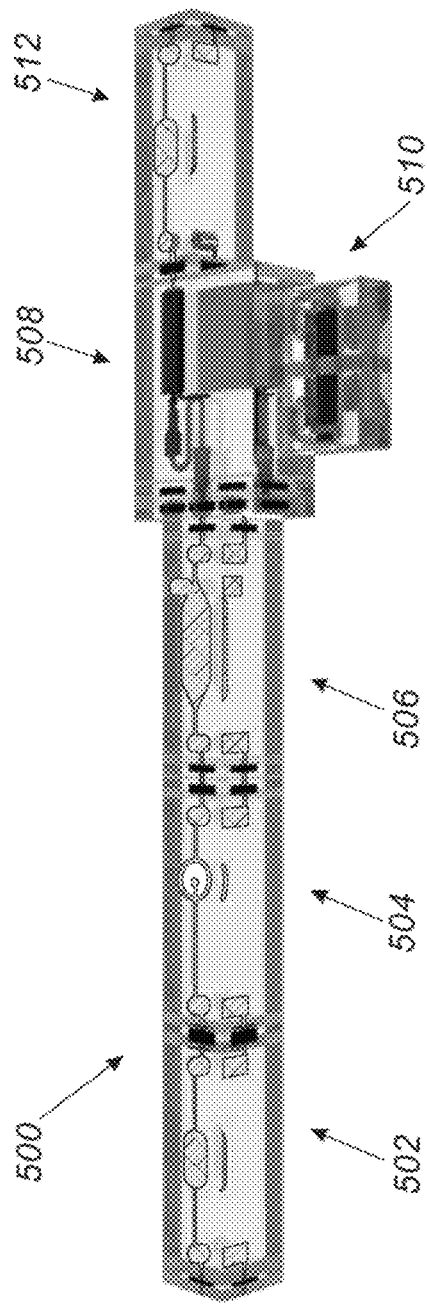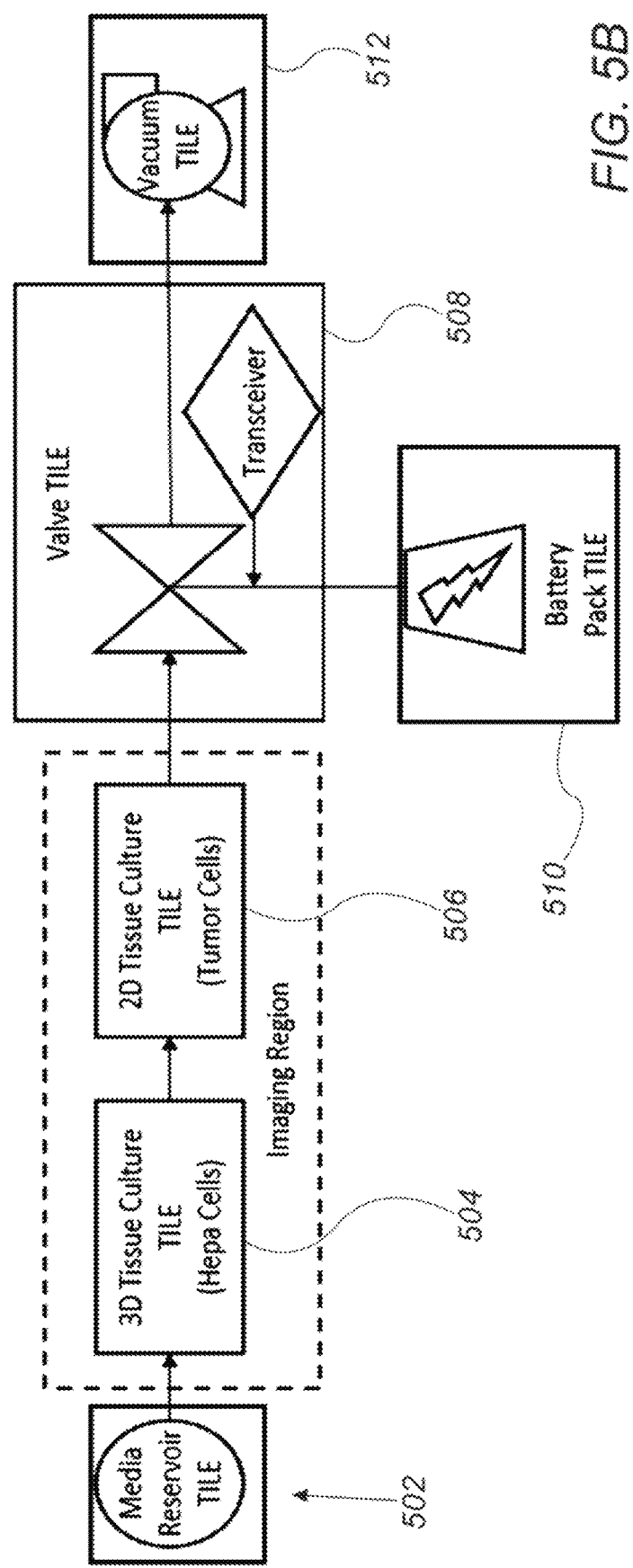
FIG. 5A
FIG. 5B

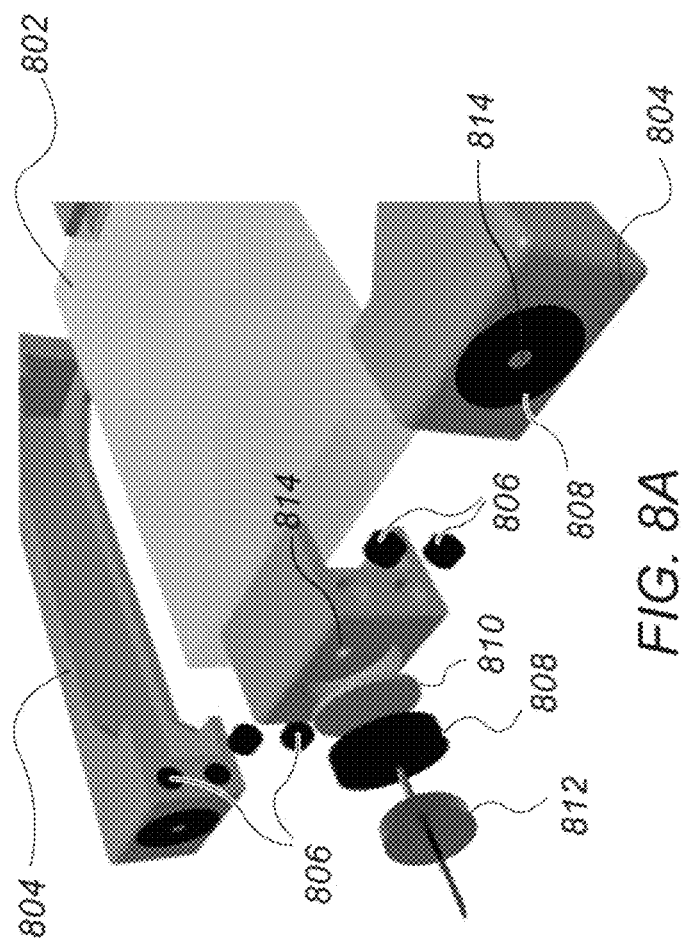
FIG. 8A
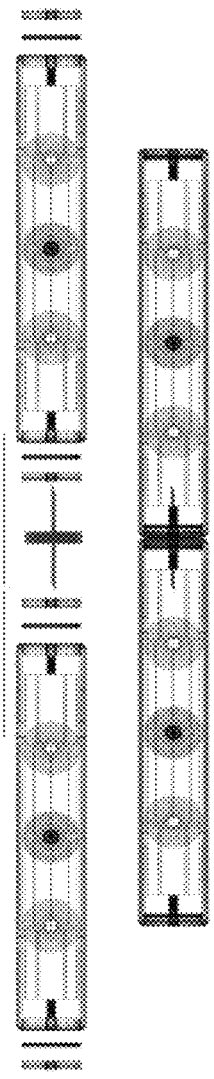
FIG. 8C
FIG. 8B

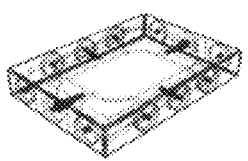 
FIG. 9A
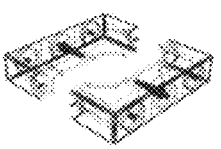 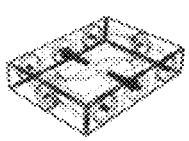  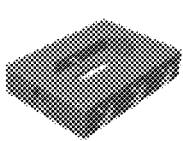
FIG. 9B
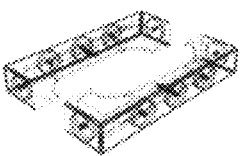 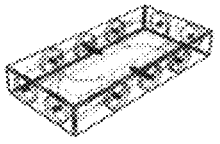 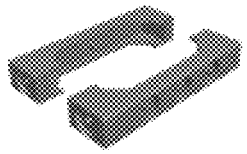 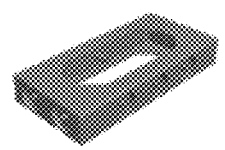
FIG. 9C
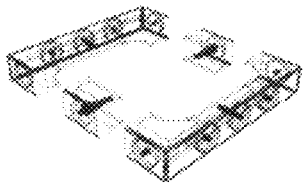 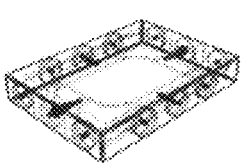 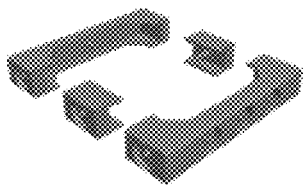 
FIG. 9D
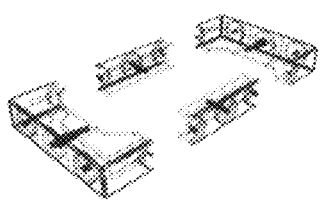 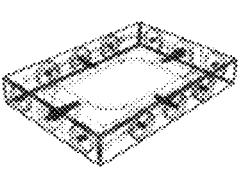 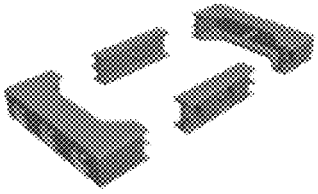 
FIG. 9E
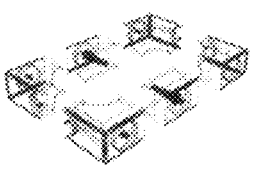 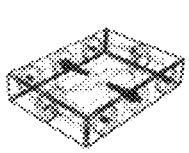 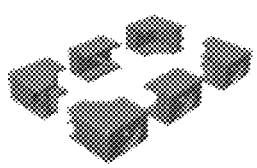 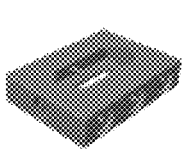
FIG. 9F
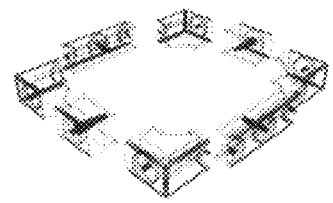 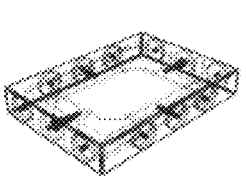 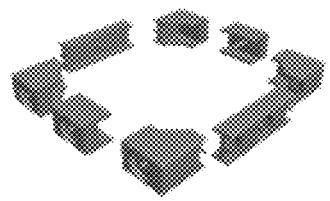 
FIG. 9G

PLANAR MODULAR MICROFLUIDIC SYSTEM

TECHNICAL FIELD

The present disclosure generally relates to planar modular microfluidic modules and systems that enable multi-organ systemic interactions.

BACKGROUND

Microfluidic cell-based models, also known as 'organs-on-chips', are being developed for various in vitro cell-based testing applications due to their ability to mimic physiological tissue architecture or environment and to enable fluid flow to facilitate delivery of reagents and drugs to the cells. Current microfluidic cell models are used for conducting various types of cell-based assays, including acute toxicity response ($IC_{50}$ of drugs), efficacy or potency of therapeutics ($EC_{50}$ of drugs), chronic drug response, combinatorial effects of drugs or cytokines, and pharmacodynamics and pharmacokinetics (PD/PK). In addition to the microfluidic cell or tissue models, other microfluidic functional units, such as pumps, valves, bubble traps, and gradient generators, must be included into the microfluidic system in order to sustain perfusion culture of the cells/tissues and to deliver reagents (e.g., drugs, and buffers) for conducting the assay.

To date, microfluidic systems for conducting cell-based assays are mostly designed and operated as a complete integrated system, which are difficult to develop and operate. Since the integrated system designs are often lab or company specific, it is difficult to standardize the microfluidic cell-based assays across different laboratories, which limits practical use by end-users e.g., pharmaceutical companies, biologists, or clinical diagnostic labs. In addition, since the integrated systems already include all of the microfluidic cell or tissue types and all microfluidic functional units that are required per a certain testing application, each testing application requires a pre-designed integrated microfluidic system, with no way to change any of the components once assembled. Furthermore, microfluidic systems should be compatible with existing imaging systems, e.g., high content screening (HCS) systems, fluorescence microscope, confocal microscope, etc., which are designed to accept microscope slides and micro-well plates, in order to automate image acquisition and analysis.

There is therefore a need for a system and method for enabling modularity and diversity when assembling microfluidic systems.

SUMMARY

The present disclosure provides a system including a plurality of planar modular microfluidic modules, each module comprising a base layer, a fluidic layer, configured to be attached to and on top of the base layer, a physical connector configured to enable lateral connection between adjacent modules, whereby the physical connector is positioned on at least one side of the module, and a fluidic connection port configured to enable fluid flow connection between adjacent modules, whereby the fluidic connection is located within the physical connector.

In some embodiments, the planar modular microfluidic module may further comprise conduction nodes configured to provide integrated circuitry for electrical connection or data transfer between adjacent modules.

In some embodiments, the base layer may comprise circuitry or electronic components.

In some embodiments, the fluidic layer may comprise fluidic channels for fluid flow between adjacent modules.

In some embodiments, the planar modular microfluidic module may further comprise a top layer configured to be bonded to the fluidic layer, such to conform the size of the module to standardized size.

In some embodiments, the planar modular microfluidic module may further comprise a plug located on one side of the module, the plug configured to prevent flow there through.

In some embodiments, the module may comprise more than one physical connector located on at least one side of the module and arranged in a diagonal manner such to enable an imaging system to image each fluidic connection port of the more than one physical connector.

In some embodiments, the module may comprise more than one fluidic connection port arranged in a diagonal manner within at least one physical connector such to enable an imaging system to image the fluidic channels. In some embodiments, the physical connector may be a magnetic connector. In some embodiments, the fluidic layer may be made of Polydimethylsiloxane (PDMS), polymethylmethacrylate (PMMA), Polyethylene terephthalate (PET), polystyrene, polycarbonate, clear 3D printed resin, glass, or any combination thereof. In some embodiments, the base layer may be made of Polydimethylsiloxane (PDMS), polymethylmethacrylate (PMMA), Polyethylene terephthalate (PET), polystyrene, polycarbonate, clear 3D printed resin, glass, or any combination thereof, with the addition of neodymium or any other strong magnet.

In some embodiments, the module may be configured to be imaged by a fluorescence microscope, a confocal microscope, or high content screening (HCS) imaging systems. In some embodiments, the module may be configured to connect to any type of fluidic connector.

In some embodiments, the fluidic connector may be selected from a group consisting of: a four-way connector configured to enable fluid flow through four outlets, a three-way connector configured to enable fluid flow through three outlets, a two-way 'L' shaped connector configured to enable fluid flow through two outlets positioned perpendicularly to one another, and a two-way straight connector configured to enable fluid flow through two outlets positioned along one line.

According to some embodiments, the present disclosure provides a system including a plurality of planar modular microfluidic modules, each module comprising a base layer, and a fluidic layer, whereby the fluidic layer may be configured to be attached to and on top of the base layer, such that the base layer and the fluidic layer may be configured to create a single basic module. The module may further comprise a jacket configured to cover the single basic module around its lateral sides, in order to provide sturdiness to the single base module and create a jacket covered module, whereby the jacket may comprise a physical connector configured to enable lateral connection between adjacent modules, the physical connector positioned on at least one lateral side of the jacket covered module, and a fluidic connection port configured to enable fluid flow connection between adjacent modules, whereby the fluidic connection may be located within the physical connector of the jacket.

In some embodiments, the physical connector may be a magnetic connector.

In some embodiments, the jacket may comprise septa positioned between the jacket and the physical connector, the septa may be configured to maintain leak-proof connections between adjacent modules. In some embodiments, the jacket may comprise a needle adaptor configured to enable fluidic connection between adjacent modules.

In some embodiments, the jacket may comprise a single jacket piece configured to house the module with the addition of solidified liquid PDMS positioned in between the basic module and the jacket. In some embodiments, the jacket may comprise a plurality of jacket pieces connected to one another around the basic module. In some embodiments, the plurality of jacket pieces are connected to one another via inner magnetic connectors located within each of the plurality of jacket pieces.

In some embodiments, the jacket may further comprise circuitry configured to provide electrical connection between adjacent modules. In some embodiments, the module may be capable of performing a biological or an engineering function. In some embodiments, a plurality of modules may be connected to one another, and the order and type of the plurality of modules may be interchangeable. In some embodiments, the module may be configured to be imaged by a fluorescence microscope, a confocal microscope, or high content screening (HCS) imaging systems.

In some embodiments, the jacket covered module may comprise at least two physical connectors located on at least one side of the jacket covered module and arranged in a diagonal orientation. In some embodiments, the jacket covered module may comprise at least two fluidic connection ports arranged in a diagonal manner within the at least two physical connectors such to enable an imaging system to image fluidic channels created by the fluidic connection ports.

According to some embodiments, the present disclosure provides within a planar modular microfluidic module, an at least one microfluidic connector comprising an at least one physical connector configured to enable lateral connection between adjacent planar microfluidic modules, said physical connector positioned on at least one side of the planar modular microfluidic module; and an at least one fluidic connection port configured to enable fluid flow connection between adjacent planar microfluidic modules, wherein said at least one fluidic connection port is located within said at least one physical connector.

In some embodiments, the microfluidic connector further comprises an at least one conducting node for conducting an electrical charge or data.

The present disclosure provides a method for manufacturing a planar modular microfluidic module, the method may include providing a microfluidic basic module comprising a base layer, and a fluidic layer, providing a jacket, whereby the jacket may comprise magnetic connectors, fluidic connections ports and circuitry, and fitting the jacket around the microfluidic basic module in order to provide modularity, protection and sturdiness to the microfluidic basic module, thereby creating a jacket covered module.

BRIEF DESCRIPTION OF THE DRAWINGS

Some non-limiting exemplary embodiments or features of the disclosed subject matter are illustrated in the following drawings.
In the drawings.

FIGS. 1F-1I are schematic illustrations of magnetic connectors and their attachment to microfluidic modules, according to embodiments of the disclosure;

FIG. 2A-2D are schematic illustrations of different types of single modular microfluidic modules, in front/back, lateral, bottom and top views, according to embodiments of the disclosure;

FIGS. 5A-5B are schematic illustrations of a multiple modular microfluidic functional modules connected together to modify the flow from one unit to the next to create unidirectional perfusion flow in an automated wireless manner, according to embodiments of the disclosure;

FIGS. 8A-8C schematically illustrate connections between a modular microfluidic module and a jacket, according to embodiments of the disclosure;

FIGS. 9A-9G are schematic illustrations of jackets comprised of different numbers of pieces, according to embodiments of the disclosure;

Figure 1A:
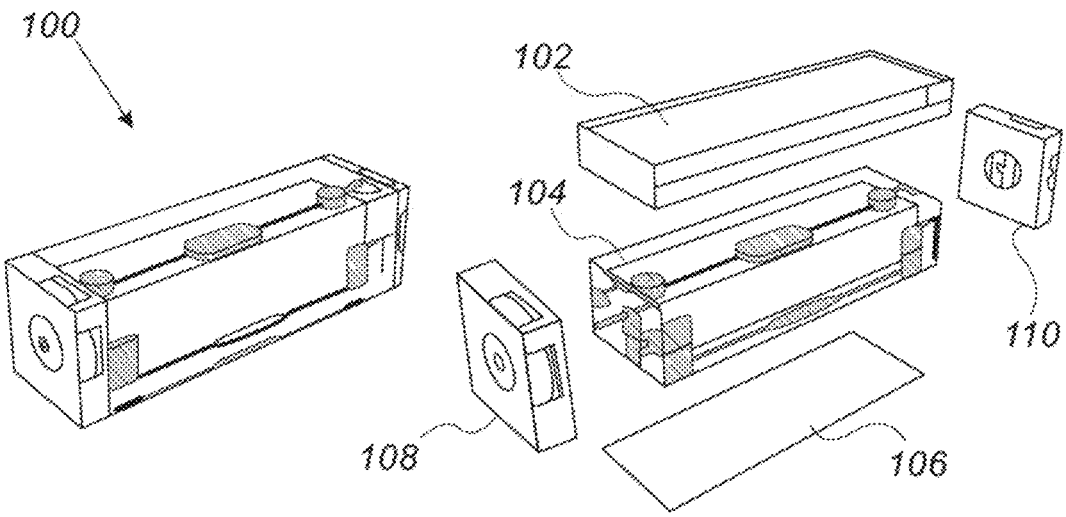
FIGS. 1A-1C are schematic illustrations of a single modular microfluidic module, in perspective, lateral and top views, respectively, according to embodiments of the disclosure.

With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

Identical or duplicate or equivalent or similar structures, elements, or parts that appear in one or more drawings are generally labeled with the same reference numeral, optionally with an additional letter or letters to distinguish between similar entities or variants of entities, and may not be repeatedly labeled and/or described. References to previously presented elements are implied without necessarily further citing the drawing or description in which they appear.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

DETAILED DESCRIPTION

In order to overcome the limitations of integrated microfluidic systems, which are commonly used to date, the present disclosure provides modular microfluidic modules and systems. These novel planar modular microfluidic systems allow easy and flexible configuration of microfluidic systems through the assembly of various standardized microfluidic modules, which perform specific functional operations applicable in cell-based assays, e.g., 2D/3D cell culture, fluid delivery (e.g., via flow connectors), pumping (e.g., via hydrostatic, peristaltic or vacuum driven pumps), flow control (e.g., via valves), concentration generators, combinatorial mixers, and bubble traps. Each microfluidic module of the present disclosure may include at least one universal fluidic connector that is capable of forming a reversible seal with any other type of module, thus allowing to establish a connection between any number of different modules at almost any orientation, while minimizing risk of contamination of the different modules.

One embodiment of the planar modular microfluidic modules may comprise a basic microfluidic module with physical connectors that enable lateral connections between adjacent modules, as well as fluidic connection ports that enable fluid connection between adjacent modules. Another embodiment of the planar modular microfluidic modules may comprise a basic microfluidic module housed within a jacket that provides sturdiness to the basic module, whereby the jacket comprises physical connectors that enable lateral connections between adjacent modules, as well as fluidic connection ports that enable fluid connection between adjacent jacket covered modules. Either of these two types of microfluidic modules may provide connectivity by and when being typically connected to modules of the same type. When a plurality of modules are connected to one another, a modular microfluidic system that may either mimic function of a single organ or mimic function of several organs of the human body and the effect of the function of one "organ" on the other "organs", may be created.

An important requirement for the successful implementation of modular organs-on-chips system is that it must be suitable to undergo high resolution imaging to observe and interrogate the phenotypes and functions of the cells growing or present in the device. Ideally, the microfluidic system should be compatible with existing imaging systems, e.g., high content screening (HCS) systems, fluorescence microscope, confocal microscope, etc., which are configured for microscope slides and micro-well plates, in order to automate image acquisition and analysis. This mandates that one side of the microfluidic systems, e.g., the side that would be imaged within HCS systems, should be between 130 to 170 µm thick so as to fall within the working distance of high magnification objectives. The overall height of the microfluidic system should also not exceed the height of a standard micro-well plate (i.e., approximately 15 mm). However, in case the microfluidic system is to be imaged by other microscopes, the height of the modules of the system should be between approximately 3 mm to 10 mm. This width constraint caused by the imaging constraint further implies that each of the modular microfluidic modules (either the basic one with physical connectors and fluidic connection ports, or the jacket covered module, which also comprises physical connectors and fluidic connection ports for connectivity between adjacent modules) comprises lateral connections instead of top-oriented connections. Thus, the modular microfluidic modules are in fact planar modular microfluidic modules.

With respect to this disclosure, modularity of the planar microfluidic modules refers to allowing easy and flexible configuration of a microfluidic system to conduct different cell-based assays for a given type of tissue chip. For Example, a tumor chip may be implemented in several different configurations: (a) a microfluidic system that may measure the dose response to get $EC_{50}$ of a cancer drug requires a tumor chip and a concentration gradient generator; (b) a microfluidic system that may determine the optimal combinations of three standard of care anti-cancer drugs for a given patient's tumor requires a tumor chip and a combinatorial mixer; (c) a microfluidic system that may determine the side effects of anti-cancer drugs on other tissues, e.g. liver, or bone marrow requires a tumor chip, a liver or bone marrow chip, a peristatic pump and connectors.

Each planar modular microfluidic module may be designed, fabricated, optimized and operated independently of the other modules, which shortens the time to develop an entire microfluidic system for conducting a particular cell based assay as compared to an integrated microfluidic system. Modular microfluidic modules are also cheaper to manufacture since each module is fabricated separately, and a plurality of modules are connected to one another only when an entire microfluidic system is required for a cell-based assay. That is, modularity of the microfluidic modules refers to the ability to choose from a variety of different modules, and the ability to assemble any types and numbers of modules in order to assemble a complete microfluidic system suitable to a wide variety of clinical and research applications.

With respect to this disclosure, the words module and brick may be interchangeable and may refer to the same basic unit, which when different types of it are connected to one another an entire cell-based assay micro fluidic system is assembled. This is due to the fact that each module may be considered as one building brick out of a variety of bricks that "builds" an entire microfluidic system.

Figure 1B:
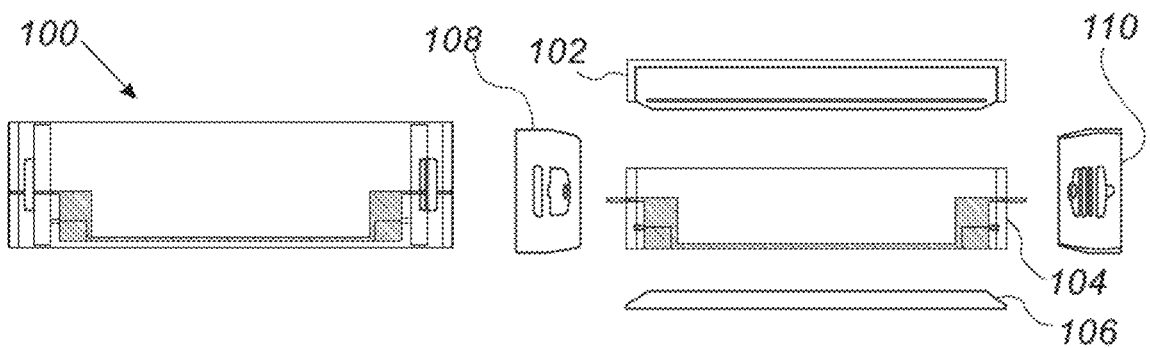
Figure 1C:
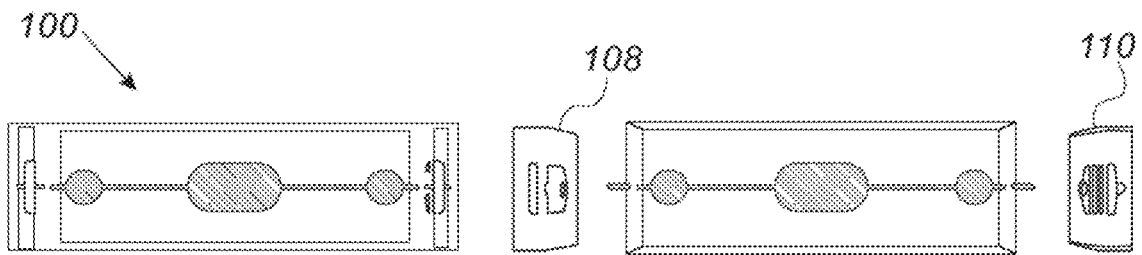

Reference is now made to FIGS. 1A-1C, which are schematic illustrations of a single modular microfluidic module 100, in perspective, lateral and top views, respectively, so according to embodiments of the disclosure. According to some embodiments, any modular microfluidic cell or module, e.g., microfluidic module 100, may be comprised of a fluidic layer 104, and a base or cap layer 106. In some embodiments, a modular microfluidic module may further comprise a top layer 102 and may comprise one or more means for stopping fluid flow. For example, module 100 may comprise a pierceable septum or a plug or a stopper in order to prevent fluid flowing through the end of module 100 where a plug is located. For example, plugs 108, 110, may be located on opposite sides of the microfluidic module in order to prevent fluid flow from one end of the microfluidic module to another, typically opposite end of the module. In other embodiments, a plug may be positioned on other sides of the microfluidic module when fluid flow is to be prevented. In yet other embodiments, a plug may be located on any of the sides of the microfluidic module. In other embodiments, when fluid flow should not be stopped, no plug is to be used as part of the microfluidic module.

According to some embodiments, top layer 102 may be configured to enable port access (e.g., cell seeding) or may be used for sizing purposes. That is, in order to manufacture a standardized microfluidic module, that may fit HCS imaging systems, the size of top layer 102, and/or the size of base layer 106 may be adjusted such to match the size of any microfluidic module to a certain standardized size. For example, a standardized height may be between 3 mm to 10 mm. Thus, depending on the complexity of the module, for example, if a module comprises multiple fluidic layers, the thickness of top layer 102 and/or base layer 106 may have to be adjusted in order to conform to the standardized height that is required for all of the planar modular microfluidic modules.

In some embodiments, fluidic layer 104 may comprise the fluidic channels (illustrated as fluidic channels 120), and base or cap layer 106 may be configured to seal the fluidic layers from one side of the assembled module, e.g., from the bottom side. In some embodiments, base layer 106 may contain circuitry or any electronic components.

In some embodiments, the plugs, e.g., plugs 108 and 110 may comprise means to enable connection between adjacent modules. For example, the plugs may comprise magnetic elements, e.g., magnets, such that adjacent modules each having plugs comprising magnetic elements, may be magnetically connected to one another. In other embodiments, the basic microfluidic module 100 that comprises fluidic layer 104 and base layer 106 may comprise at least one physical connector, e.g., a magnetic connector, located on at least one lateral side of the basic module 100, such to enable lateral connectivity between adjacent modules. In some embodiments, each or more than one of the sides of module 100 may comprise at least one connector, in order to enable connection of additional modules to almost any side of module 100. This enables modularity with respect to the order and type of a plurality of modules that create a modular microfluidic system. the order and type of modules may be interchangeable when creating a modular microfluidic system.

In some embodiments, top layer 102 and fluidic layer 104 may be made of the same materials, for example, Polydimethylsiloxane (PDMS), polymethylmethacrylate (PMMA), Polyethylene terephthalate (PET), polystyrene, polycarbonate, clear 3D printed resin, glass, or any combination thereof. In some embodiments, base layer 106 may be made of the same materials that top layer 102 may be made of, with the addition of neodymium or any other strong magnets as well as conductive wiring and circuits (resistors, capacitors, microcontrollers, sensors, etc.). In some embodiments, the plugs, e.g., plugs 108 and 110, may be made of the same materials as top layer 102 with the addition of neodymium or any other strong magnets.

According to some embodiments, the length of a microfluidic module may be between 10 to 80 mm, while the preferable length may be between 40 to 60 mm. According to some embodiments, the width of a microfluidic module may be between 10 to 50 mm, while the preferable length may be between 20 to 40 mm. According to some embodiments, the height of a microfluidic module may be between 2 to 18 mm, while the preferable length may be between 9 to 12 mm.

Figure 1D:
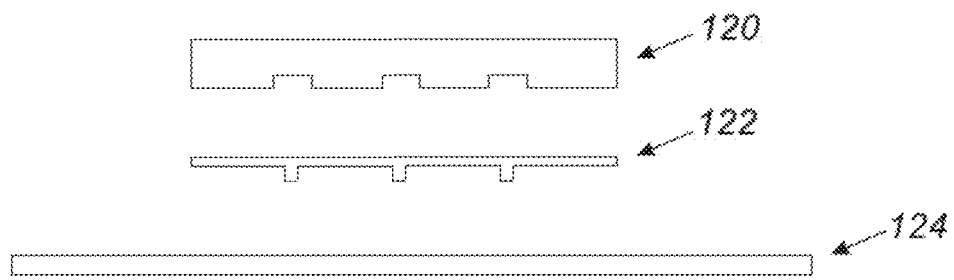
FIGS. 1D-1E are schematic illustrations of the different layers and fluidic channels of a single microfluidic module, according to embodiments of the disclosure.
Figure 1E:
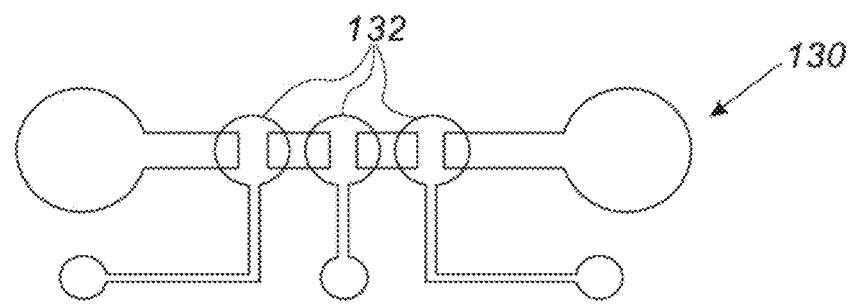
Figures 1F, 1G:
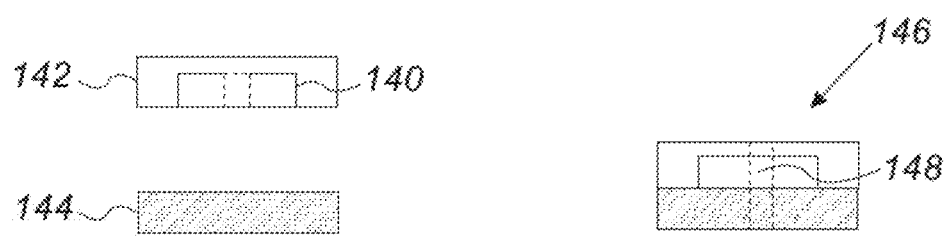

Reference is now made to FIGS. 1D-1E, which are schematic illustrations of the different layers and fluidic channels of a single microfluidic module, according to embodiments of the disclosure. According to some embodiments, individual microfluidic modules may be produced by casting Polydimethylsiloxane (PDMS) at a weight ratio of, for example, 10:1 of elastomer to curing agent on pre-existing molds. The PDMS may be then cured for four hours in 70° C. For a peristaltic pump type module, the on-chip pump module may be fabricated via irreversible bonding between a pneumatic substrate 120, a fluidic substrate 122 and a glass substrate 124 together to form a complete fluidic channel 130. The pneumatic and fluidic layers 120 and 122, respectively, may both be made of Polydimethylsiloxane (PDMS) layers, prepared by thoroughly mixing a polymer base and a curing agent (e.g., Sylgard 184, Dow Corning) at the weight ratio of 10:1. After which, the PDMS pre-polymer mixture may be degassed in a desiccator until all air bubbles are removed. After degassing, the PDMS pre-polymer mixture may be poured into both pneumatic and fluidic molds, and may be placed into the desiccator for another round of degassing. Subsequently, the PDMS pre-polymer may then be thermally cured in a 70° C. oven for four hours. The pneumatic layer 120, which may be located at the top end of the module may be plasma bonded to the fluidic layer 122, which may be located beneath pneumatic layer 120. In some embodiments, holes may be punched through the pneumatic and fluidic layers 120 and 122, respectively, in order to allow for the connection of external vacuum access, and create the inlet and outlet of a fluidic channel for fluid access (FIG. 1E). The plasma bonded layers may then be connected to a vacuum source via external tubing to ensure that the actuation valves 132 are open when being plasma bonded to either a glass substrate 124 or thin PDMS membrane (not shown), which forms the fluidic channel (FIG. 1D).

In some embodiments, with respect to microfluidic cell culture modules, gradient generator modules and connector modules, the PDMS modules may be fabricated in a similar manner and may be carefully removed from their respective molds and, together with a thin PDMS membrane may be plasma treated with oxygen using a plasma generator and may be subsequently bonded on to either a glass substrate or a thin PDMS membrane.

Reference is now made to FIGS. 1F-1I, which are schematic illustrations of magnetic connectors and their attachment to microfluidic modules, according to embodiments of the disclosure. According to some embodiments, a magnetic connector 140 for connecting adjacent modules, may be comprised of a nickel-plated neodymium ring shaped magnet (N42 6.35 mm OD×3.175 mm ID×1.5875 mm thick, K&J Magnetics, USA), which may be embedded between two layers of PDMS 142 and 144 FIG. 1E). The PDMS pre-poly mixture 142 may be degassed for removal of air bubbles, and one tea spoon of red PDMS pre-poly may be poured into a square container that forms the shape of the magnetic PDMS module. After which, the PDMS pre-polymer mixture may be thermally cured in a 70° C. oven for a minimum of four hours. The ring magnet may then be placed on top of the cured PDMS layer 142 and may be covered with clear PDMS pre-polymer layer 144, which may be allowed to cure in room temperature for a minimum of two days. The overall thickness of the magnetic connector 146 may be approximately 5 mm.

Such magnetic connectors may be bonded to the inlet and outlet of a peristaltic pump module (FIG. 1H), and a hole 148 may then be punched through the two layers on each side of the module to ensure a consistent channel for inlet and outlet (FIG. 1I). Instead of bonding to a glass slide, e.g., glass substrate 124 (FIG. 1D), the pneumatic layer 120 and fluidic layer 122 may be bonded to a thin PDMS layer 150 (FIG. 1H) to allow for punching of holes there through to create the inlet and outlet. Lastly, a thin PDMS layer may be bonded to the top of the pneumatic layer, e.g., layer 120 to seal any holes in pneumatic layer 120 such to form a complete fluidic channel. Throughout the assembly process of the magnetic connector to the planar modular microfluidic peristaltic pump module, a vacuum source should be kept active to ensure valve pads do not permanently bond to the thin PDMS.

Reference is now made to FIGS. 2A-2D, which are schematic illustrations of different types of single modular microfluidic module, in front/back, lateral, bottom and top views, according to embodiments of the disclosure. In some embodiments, each microfluidic module, e.g., module 200, may comprise a physical connector, e.g., magnetic connector 202 configured to connect between one module to another, a fluidic connection port 204 configured to enable fluidic connection between two adjacent connected modules, and conducting nodes 206 for integrated circuitry configured to provide power or energy to a module, as required for proper operation. As illustrated in the example of FIG. 2A, module 200 comprises one magnetic connector 202 on the back or front side of module 200. In some embodiments, magnetic connector 202 may comprise a single fluidic connection port 204. In some embodiments, magnetic port 202 need not comprise a fluidic connection port. In some embodiments, the magnetic ports, may be located on the back, front or lateral sides of a module. For example, FIG. 2A illustrates one of the lateral sides of module 200 comprising more than one magnetic ports, for example, magnetic ports 208, 209 and 210. Each magnetic port may have a different number of fluidic connection ports. For example, magnetic port 208 may comprise no fluidic connection port, magnetic port 209 may comprise one fluidic connection port, whereas magnetic port 210 may comprise no fluidic connection port.

In some embodiments, the bottom side of module 200 may comprise a layout of conduction nodes and integrated circuitry, whereas the top side of module 200 may comprise the fluidic channels. As illustrated, module 200 comprises one fluidic channel between the back and the front sides of module 200, and another fluidic channel between the two opposite lateral sides of module 200.

As illustrated in FIG. 2B, another module, e.g., module 220 may comprise a magnetic port 222, on the back or front side of module 200, which may comprise more than one fluidic connection ports. For example, the back or front side of module 200 may include two fluidic connection ports, e.g., fluidic connection ports 224, 225 inside a single magnetic port 222, configured to enable fluid passage along two different fluidic channels, passing between the front and the back sides of module 200. In some embodiments, each of the fluidic connection ports 224, 225 may enable a different type of fluid to pass through each of these ports, thus providing the possibility to create a more complex microfluidic system for conducting different cell-based assays. In some embodiments, multiple ports inside a single magnetic connector may be oriented horizontally (as shown in FIG. 2B) or may be oriented vertically to accommodate multiple fluidic layers. Module 200 may further comprise on its back or front side conducting nodes 226 (as shown in FIG. 2C), for conducting electrical charge or data. Module 200 may comprise, on its lateral sides, more than one magnetic connector, e.g., magnetic ports 228, 229 and 230. Each of magnetic ports 228, 229 and 230 may comprise a different number of fluidic connection ports. For example, magnetic port 228 may comprise no fluidic connection port, magnetic port 229 may comprise two fluidic connection ports, and magnetic port 230 may comprise no fluidic connection ports. Similarly, to module 200, the bottom side of module 220 may comprise a layout of conduction nodes and integrated circuitry, and the top side of module 220 may comprise the fluidic channels. As mentioned above, module 220 comprises two fluidic channels between the front and back sides of module 200, and may further comprise two fluidic channels between the two opposing lateral sides of module 220. The use of more than one fluidic channel enables the provisioning of two or more different fluids running in the same system through a single physical connector, e.g., a magnetic connector. This enables more complex microfluidic systems to be designed using a reduced number of micro fluidic modules.

In the example illustrated in FIG. 2C, a microfluidic module, e.g., module 240 may comprise more than one magnetic port on the front or back side of module 240. In some embodiments, the plurality of magnetic connectors (each with either no, a single or more than one fluidic port inside) may be oriented diagonally (as shown in FIG. 2C), vertically, or horizontally depending on the number of fluidic layers required.

In the example illustrated in FIG. 2D, multiple magnetic connectors may be implemented on each side of a module with a variable number of fluidic ports inside each magnetic connector. The magnetic connectors may be oriented diagonally (as shown in FIG. 2D), vertically, or horizontally depending on the number and complexity of the fluidic layers required. According to FIG. 2D, three magnetic ports are present on the back or front side of module 260. Each of the three magnetic ports comprises a different number of fluidic ports. According to FIG. 2D the lateral sides of module 260 may further comprise multiple magnetic ports each comprising a different number of fluidic ports, which may be oriented either horizontally (as shown in FIG. 2D) or may be oriented vertically to accommodate multiple fluidic layers. Accordingly, the fluidic channels are illustrated on the top side of module 260. The horizontal and diagonal orientations of the ports may enable the observer using an existing imaging device to maximize visibility of the fluidic channels. Thus, it is preferred that the orientation of the fluidic ports is such that they do not overlap from the vertical perspective, though it is contemplated that under some alternative embodiments vertical overlap of the ports may be useful in some cases. According to some embodiments, additional sensors and electrical components may be placed on either side of the modules depending on need or requirement. For example, as shown in FIGS. 2A-2D electrical components along with electrical circuitry may be placed at the bottom side of each of modules 200, 220, 240 and 260.

Reference is now made to FIGS. 3A-3D, which are schematic illustrations of different connectors in perspective, front, top and side views, according to embodiments of the disclosure. According to some embodiments, a planar modular microfluidic system may comprise various types of connectors, which may enable easy fluidic connection between adjacent planar microfluidic modules. Such connectors may also dictate the direction of fluid flow between modules assembled as part of a modular microfluidic system. That is, the connector modules or bricks may be used for making fluidic circuits when combined with other microfluidic functional modules.

Figures 3A, 3B, 3C, 3D:
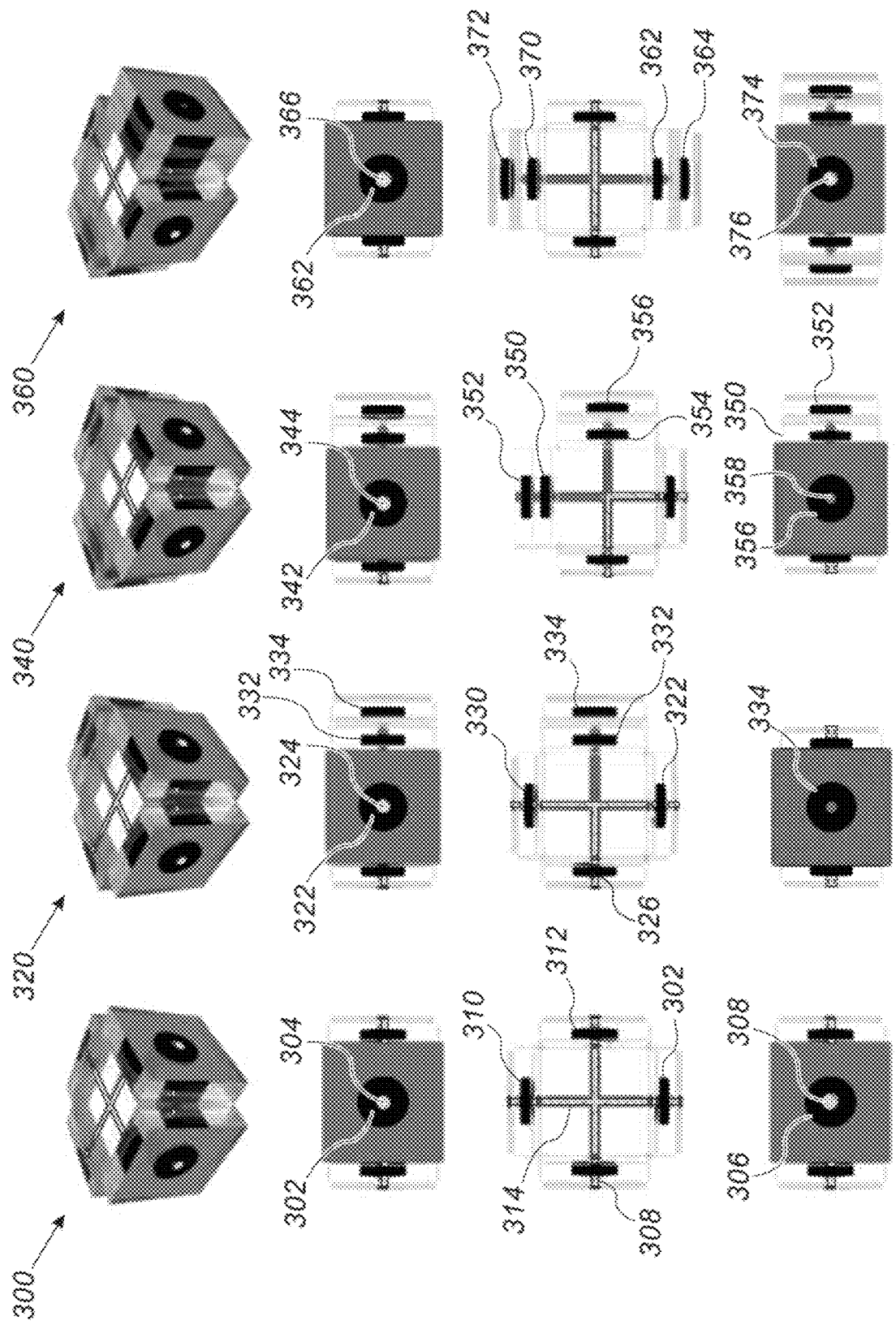
FIGS. 3A-3D are schematic illustrations of different connectors in perspective, front, top and side views, according to embodiments of the disclosure.

For example, FIG. 3A, schematically illustrates a four-way connector 300. Such a four-way connector may enable passage of fluid to each of the four sides of the connector, thereby such a four-way connector may be implemented, for example, at an "intersection" of a microfluidic system where fluid is required to flow to four different directions. That is, four-way connector 300 may be configured to enable fluid flow via fluidic channel 314 through four outlets. Connector 300 may comprise a magnetic port on each of its sides. For example, magnetic port 302 may be positioned on the front side of connector 300. Magnetic port 302 may comprise at least one fluidic port, e.g., fluidic port 304, though any other number of fluidic ports may be implemented within magnetic port 302. Connector 300 may comprise additional magnetic ports, e.g., magnetic ports 306, 310, 312, whereby each of these magnetic ports may comprise at least one fluidic port. For example, one of the sides of connector 300 may comprise magnetic port 306, which may comprise fluidic port 308.

In the example illustrated on FIG. 3B, a three-way 'T.' shaped connector 320 is provided. The three-way or 'T' shaped connector 320 may be positioned in a 'T' shaped interconnection of a microfluidic system. The three-way connector 320 may, be configured to enable fluid flow through three outlets. The three-way or 'T' shaped connector 320 may comprise a magnetic port (e.g. 322, 326, 330, 332) on each of its four sides, however, unlike connector 300, one of the magnetic ports of connector 320 includes a stopper 334 in addition to a magnetic port 332. The stopper 334 may be used in order to disable fluid flow there through, thereby creating the tree-way connector 320. The addition of stopper 334 onto magnetic port 332 prevents fluid flow through the fluidic port 324 of magnetic port 332, since stopper 334 does not comprise a fluidic port.

In some embodiments, a plug or stopper, such as plug 334 may not comprise a fluidic port, however, it may comprise a magnetic element in order to provide a magnetic connection between adjacent modules, which mays be required for other purposes besides fluid connection. The shape of the magnetic element of the plugs may be a disc with a hole (e.g., a donut), similar to the shape of a magnetic port that comprises a fluidic port, or it may be in the shape of a disc with no hole, a square, a rectangle and so on. In case a disc shape is implemented, the diameter of the circular magnetic element may be of approximately 5 mm.

In the example illustrated in FIG. 3C, a two-way 'L' shaped connector 340 is provided. Two-way connector 340 may be configured to enable fluid flow through two perpendicular outlets. A two-way 'L' shaped connector 340 is manufactured by adding a stopper to two adjacent sides of connector 340, such to stop fluid flow in those two adjacent sides. For example, connector 340 may comprise four sides each comprising a magnetic port (e.g. 342, 350) and each magnetic port may comprise at least one fluidic port (e.g. 344, 358). However, two of the sides of connector 340 may comprise stopper or plugs; magnetic port 350 may be accompanied by stopper or plug 352, and magnetic port 354 may be accompanied by stopper 356. Stopper 352 and stopper 356 may ensure no fluid passage there through.

FIG. 3D illustrates a 2-way straight connector 360, which may comprise two plugs or stoppers located on two opposing sides of connector 360, in order to enable fluid flow along a straight line. Two-way connector 360 may be configured to enable fluid flow through two outlets positioned along the same line. As such, connector 360 may comprise four magnetic ports (e.g. 362, 374) each located at a different side of connector 360. In addition, two opposing sides of connector 360 may comprise magnetic ports, e.g., magnetic ports 370 and 362, which may have attached plugs or stoppers 372 and 364, respectively. Stopper 364 may disable fluid flow there through, and plug 372 may prevent fluid flow there through however, fluidic port 376 of magnetic port 374, and the fluidic port 366 of magnetic port 362 may allow fluid flow there through.

According to some embodiments, the various connectors may be comprised of the same basic connector module, which may be combined with a plug/stopper piece that may be used to create the four different types of connectors according to the number and location of the plug/stopper. In some embodiments, each of the magnetic inter-connectors or ports of each of the four types of connectors may comprise more than one fluidic port.

Figure 4A:
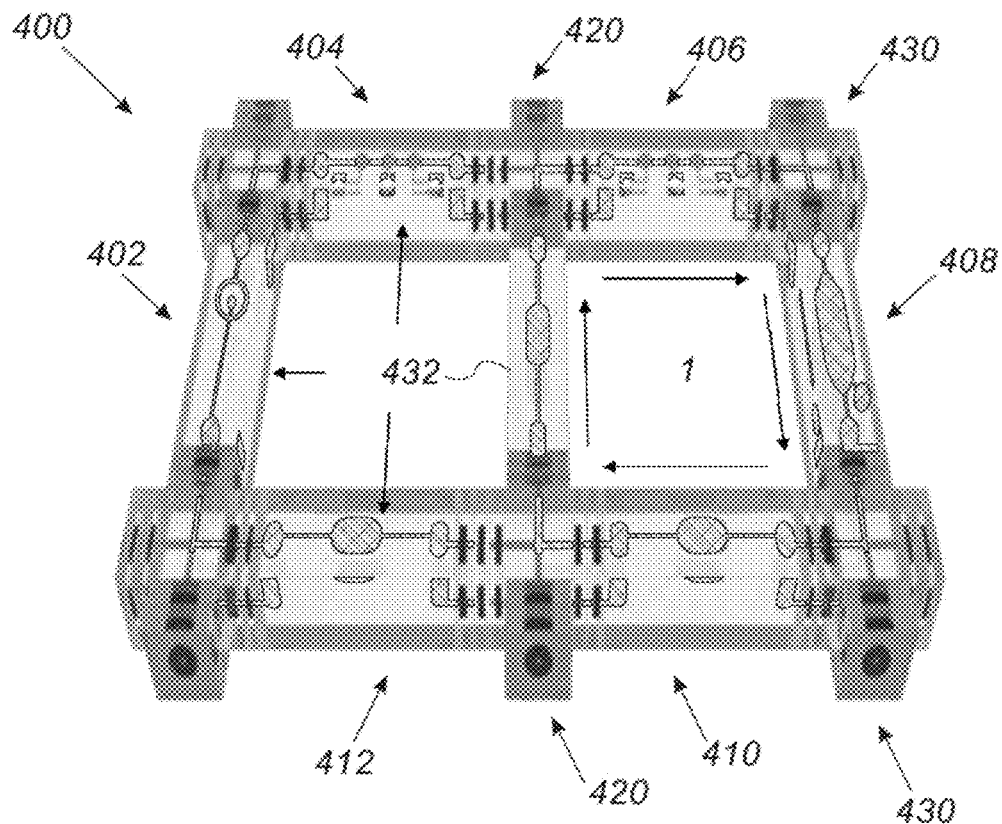
FIGS. 4A-4B are schematic illustrations of two modular microfluidic systems, which incorporate different microfluidic connector units, according to embodiments of the disclosure.
Figure 4B:
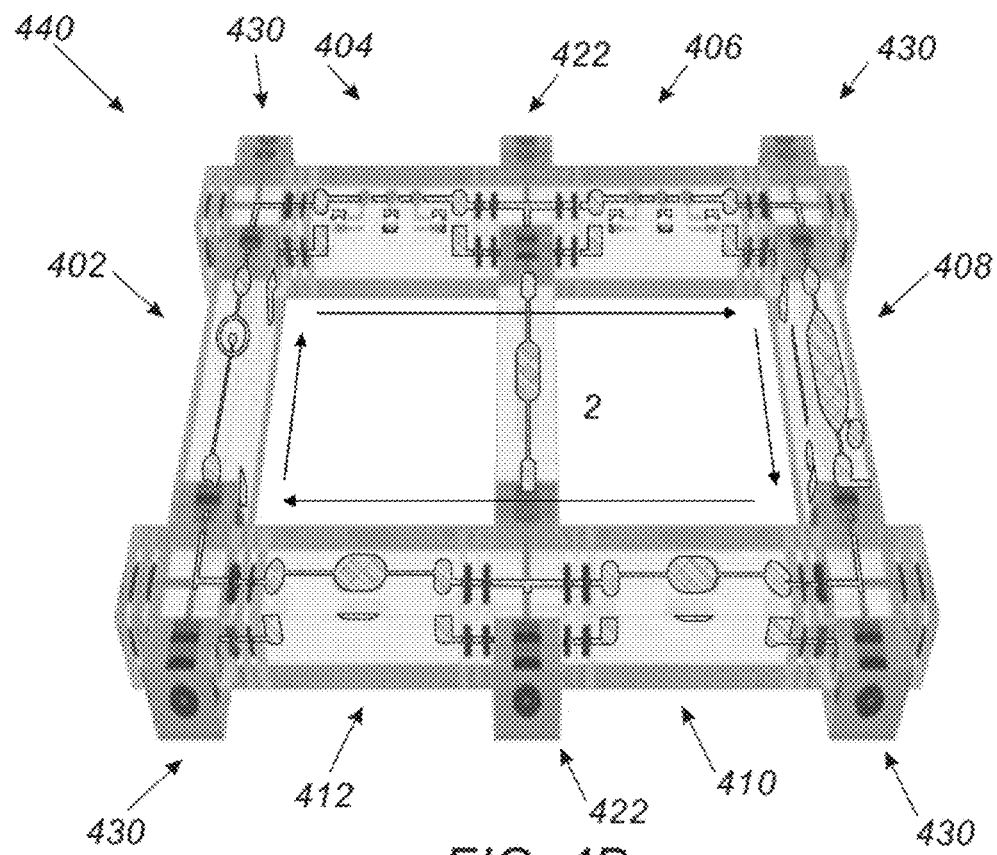

Reference is now made to FIGS. 4A-4B, which are schematic illustrations of two modular microfluidic systems, which incorporate different microfluidic connector units and microfluidic modules, according to exemplary embodiments of the disclosure. As can be seen in FIGS. 4A and 4B, modular microfluidic system 400 and modular microfluidic system 440 may comprise similar microfluidic functional units to achieve circulatory flow. For example, systems 400 and 440 may comprise a 3D Tissue culture unit 402 (which may contain liver cells), a peristaltic pump unit 404, peristaltic pump unit 406, 2D tissue culture unit 408, which may contain tumor cells; media reservoir unit 410, which may contain the cell culture media to be circulated; and media reservoir unit 412, which may contain the cell culture media to be circulated. In some embodiments, peristaltic pump units, such as peristaltic pump unit 406, are considered an "engineering" brick as its function is the driving force that pumps media through the fluidic circuit. The media reservoir units and 2-way connector units are also considered engineering bricks used to control flow. The 2D tissue culture unit is considered a "biological" brick and contains one of the tissue types (e.g., tumor cells) used within the circuit. These tumor cells may represent a live tumor growing in the human body that is sustained by the perfusion flow of nutrients within the fluidic circuit.

According to some embodiments, modular microfluidic systems make it possible to modify the flow from one module to the next by the ability to change the types of connectors along systems 400 and 440, and thus to enable modularity in the function of each system, specifically modularity in the fluid flow direction, thereby dictating which units are taking part in the circuit.

For example, system 400 comprises a two-way 'L' shaped connector 420 at the four corners of system 400. In addition, system 400 comprises a two-way 'L' shaped connector 430 between peristaltic pump unit 404 and peristaltic pump unit 406, and a wo-way 'L' shaped connector 430 between media reservoir unit 410 and media reservoir unit 412. The use of two-way 'L' shaped connectors 430 located in the above-mentioned locations, in fact disables passage of fluid along the main square structure of system 400 and only enables fluid flow along 'Loop 1', which is created by two two-way 'L' shaped connectors 430, peristaltic pump unit 406, 2D tissue culture unit 408, media reservoir unit 410, media reservoir unit 432 and two 'L' shaped connectors 420. In such case, some of the microfluidic units of system 400 are in standby state since fluid is prevented from passing there through. For example, fluid does not reach peristaltic unit 404, 3D tissue culture unit 402 nor media reservoir unit 412. This example of fluid flowing through 'Loop 1' contains the circulating cell culture media, and the tumor cells in 2D cell culture unit 408 are in fact grown separately away from any other tissue type (e.g., separately of liver cells grown in 3D tissue culture 402). When a cancer drug is introduced into Loop 1, whatever response the tumor cells exhibit will be physiologically irrelevant since drugs are normally first metabolized by the liver in the human body before they can react with the tumor cells.

On the contrary, system 440 incorporates one two-way straight connector 422 located between peristaltic pump 404 and peristaltic pump 406, and another two-way straight connector 422 located between media reservoir unit 410 and media reservoir unit 412. Accordingly, fluid flow is enables along the main square structure of system 440, i.e., fluid flow is enabled through 'Loop 2'. 'Loop 2' is created by four corner positioned two-way 'L' shaped connectors 430, peristaltic pump unit 404, peristaltic pump unit 406, 2D tissue culture unit 408, media reservoir unit 410, media reservoir unit 412 and two straight two-way connectors 422. Such operation of system 440 disables fluid flow through media reservoir unit 432 alone. This example of fluid flowing through 'Loop 2' contains circulating media between two different tissue types: the tumor cells in the 2D tissue culture unit 408 and the liver cells contained in the 3D tissue-culture unit 402. 'Loop 2' is achieved simply by switching two two-way 'L' shaped connectors 420 in the middle of the flow of the circuit to two two-way straight connectors 422. In system 440, the liver cells (located in 3D tissue culture unit 402) may process any compounds or drugs that are pumped through the circuit and may release different compounds/metabolites that may in turn flow to the tumor cells (located in the 2D tissue culture unit 408) in the fluidic circuit. The response that the tumor cells exhibit over time to the metabolized drugs is now more physiologically relevant and closer to mimicking in-vivo responses to drugs in the human body.

It should be noted that the microfluidic functional units and the microfluidic connector units are all connected via lateral connections thus creating planar modular microfluidic systems, which may be easily and conveniently imaged using HCS systems. These examples of systems 400 and 440 illustrate the numerous possibilities of using diverse microfluidic functional units and microfluidic connector units in order to assemble many types of planar modular microfluidic systems, in accordance with the exemplary embodiments of the present disclosure.

Reference is now made to FIGS. 5A-5B, which are schematic illustrations of a multiple modular microfluidic functional modules connected together to modify the flow from one unit to the next to create unidirectional perfusion flow in an automated wireless manner, according to embodiments of the disclosure. FIGS. 5A-5B illustrate an example of microfluidic system 500 comprising multiple modular bricks connected together to modify flow from one module to another adjacent module.

In some embodiments, system 500 may comprise six unique modules connected to achieve unidirectional vacuum-driven perfusion flow. System 500 may comprise two biological type bricks, e.g., 3D tissue culture unit 504, which may contain liver cells, and 2D tissue culture unit 506, which may contain tumor cells, and four engineering type bricks, e.g., media reservoir unit 502, valve unit 508, battery unit 510 and vacuum unit 512. Vacuum unit 512 may comprise a chamber with low pressure, media reservoir unit 502 may comprise liquid cell culture media at (or slightly above) atmospheric pressure, valve unit 508 may serve as a gate to control the flow rate, and battery unit 510 may provide power to the micro-valve in valve unit 508 and circuitry. Flow within this fluidic circuit of system 500 may be driven by the difference in pressure between vacuum unit 512 and media reservoir unit 502, as fluid flow naturally moves from a high[er] pressure region to a low[er] pressure region.

The different bricks or modules may be connected to one another along a straight line with flow moving from the media reservoir unit 502 to the vacuum unit 512. The advantage of using a valve unit 508 and vacuum driven flow is that no external wires or tubing is necessary. The valve unit 508 may comprise an on-board microcontroller and a micro-valve, which may be controlled wirelessly via commands sent through a master controller. FIG. 5B illustrates an exemplary flow diagram of the connected microfluidic bricks of FIG. 5A. The imaging region is shown inside the dotted-line box. That is, the region of system 500 that is being imaged comprises the biological type bricks, e.g., 3D tissue culture unit 504, and 2D tissue culture unit 506. Due to the fact the system 500 is a planar modular microfluidic system, and that connections between modules are lateral connections (and not top-oriented), imaging via HCS systems may be enabled.

Figure 6:
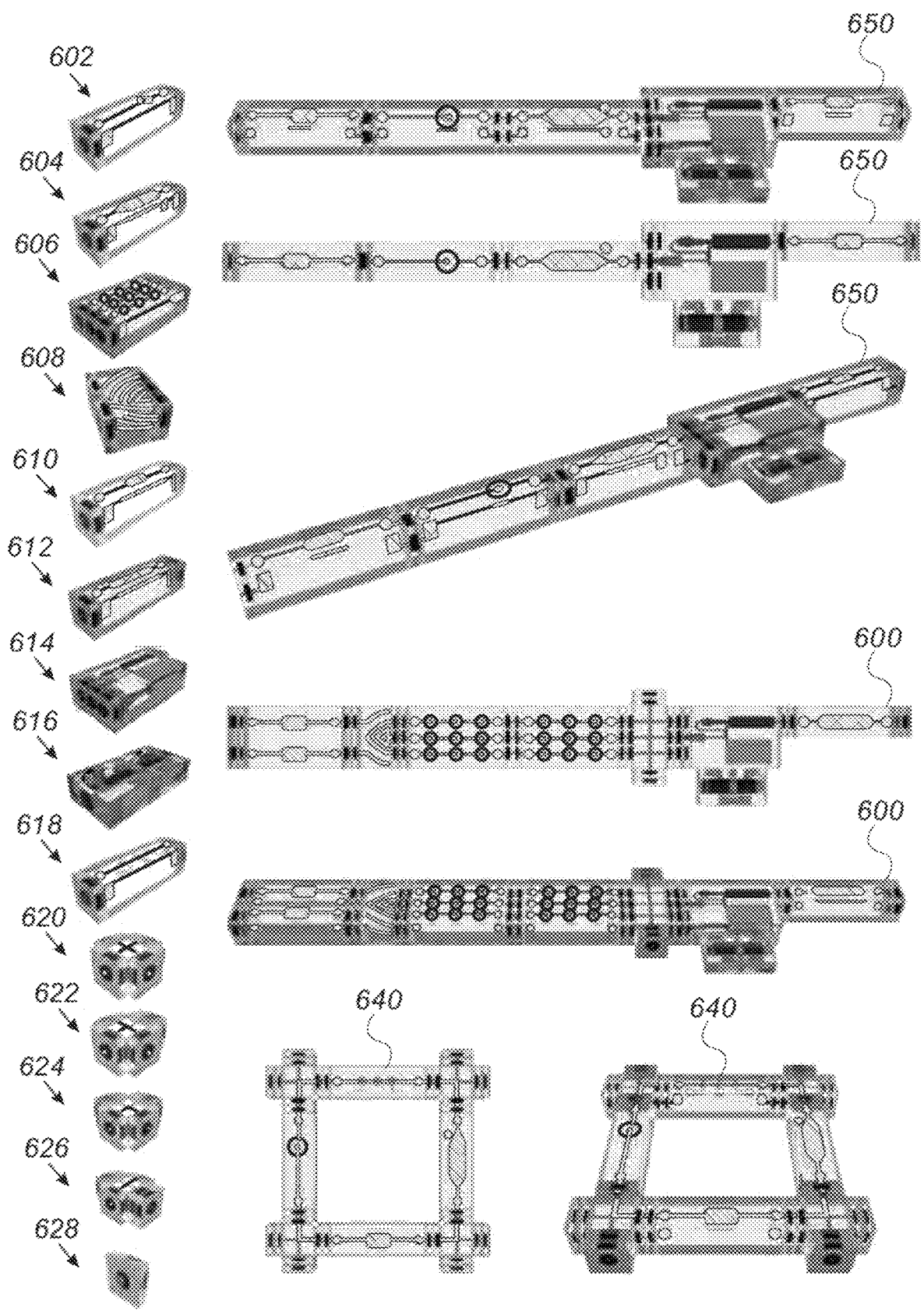
FIG. 6 schematically illustrates different modular multifunctional microfluidic modules and their possible implementation as part of different modular microfluidic systems, according to embodiments of the disclosure.

Reference is now made to FIG. 6, which schematically illustrates different modular multifunctional microfluidic modules and their possible implementation as part of different modular microfluidic systems, according to embodiments of the disclosure. As can be seen in FIG. 6, planar modular microfluidic systems according to the present disclosure may comprise a variety of microfluidic functional modules. For example, there may be several biological type modules, for example, tissue culture modules, e.g., 3D tissue culture module 602, 2D tissue culture module 604 and multiplex 2D/3D tissue culture module 606. Another type of modules may be engineering type, e.g., gradient generator module 608, media reservoir module 610, vacuum unit 612, valve unit 614, battery pack unit 616, and peristaltic pump unit 618. As described hereinabove with respect to FIGS. 3A-3D, modular microfluidic systems may further comprise four types of connector units, e.g., four-way connector unit 620, three-way connector unit 622, two-way 'L' shaped connector unit 624, and two-way straight connector 626. In addition, a plug or stopper 628 may also be implemented as necessary to control fluid flow or lack of flow.

Each of these microfluidic modules, connectors and plugs may be implemented to be part of planar modular microfluidic systems, while applying lateral connections between the various modules. For example, modules 602 (3D tissue culture), 604 (2D tissue culture), 610 (media reservoir), 612 (vacuum), 614 (valve) and 616 (battery pack) may be part of a planar modular microfluidic system 650 for drug bioactivation studies, similar to system 500 illustrated in FIGS. 5A-5B. Another example may be implementing modules 610 (media reservoir), 608 (gradient generator), 606 (multiplex 2D/3D tissue culture), 614 (valve), 612 (vacuum) and 616 (battery pack) for assembling a planar modular microfluidic system 600 for multiplexed drug screening. Yet another example may be incorporating modules 602 (3D tissue culture), 604 (2D tissue culture), 610 (media reservoir), 618 (peristaltic pump) and several connectors such as 624 and 626, along with plugs 628, thereby assembling a system 640, which may be similar to systems 400 and 440, as illustrated in FIGS. 4A-4B.

Figure 7C:
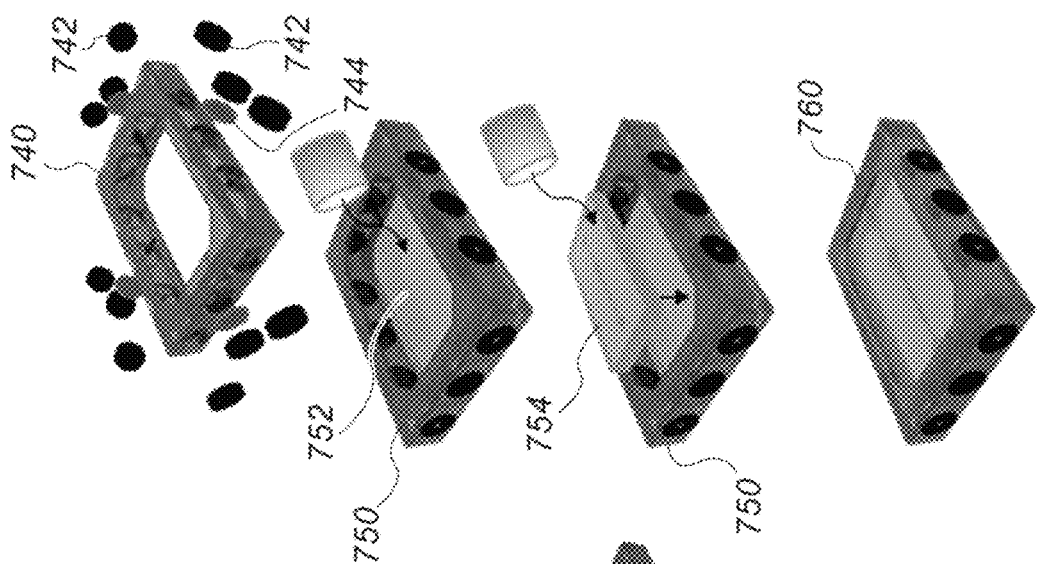
FIGS. 7A-7C are schematic illustrations of jacket pieces snapped together when connected to a single modular microfluidic module, jacket pieces snapping together with a magnetized microfluidic module, and a microfluidic module placed inside a single jacket piece, respectively, according to embodiments of the present disclosure.
Figure 7B:
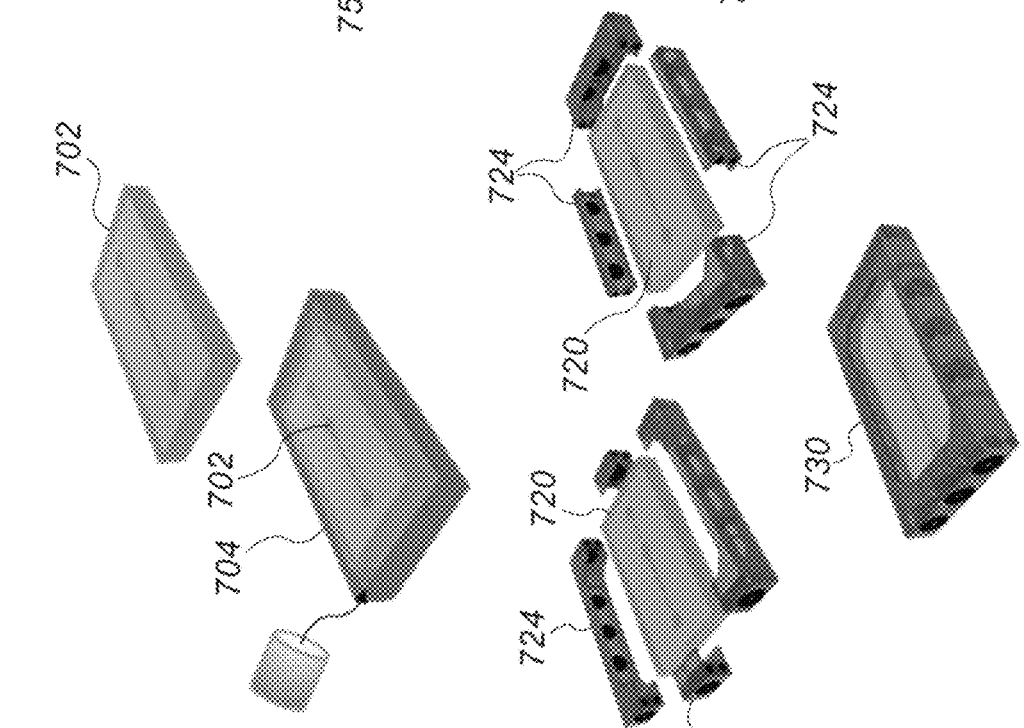
Figure 7A:
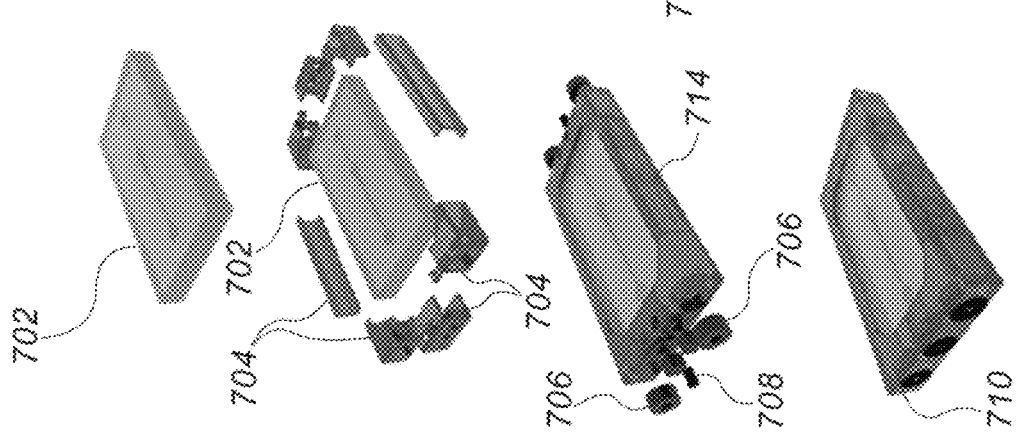

Reference is now made to FIGS. 7A-7C, which are schematic illustrations of jacket pieces snapped together when connected to a single modular microfluidic module, jacket pieces snapping together with a magnetized microfluidic module, and a microfluidic module placed inside a single jacket piece, respectively, according to embodiments of the present disclosure. According to some embodiments, when a planar modular microfluidic system comprises a large number of modules connected to one another, the magnetic connection between the modules or bricks via the magnetic ports is not sufficiently stable and additional sturdiness is required. Thus, each microfluidic module may comprise an additional element, which may cover at least four sides of the microfluidic module, and may enhance the strength of the system to maintain connections between all modules of the system. This additional strengthening element may be a jacket like element. The jacket may enhance sterility, ensure all modules are connected to the same plane, enable easy reversible connections with subsequent modules, and may enhance protection and robustness of the modules, which are typically made of PDMS.

According to the present disclosure, there are three configurations by which to connect the jacket to the microfluidic module. The configuration of connection between the jacket and the microfluidic module illustrated in FIG. 7A comprises a plurality of individual pieces 704 of the jacket, which may physically connect to one another around the brick or module 702 (the brick is made of polydimethylsiloxane (PDMS)), thus cradling the brick and forming a housing around the brick. In some embodiments, the jacket pieces may connect to one another via snaps. Once the jacket pieces 704 are connected together, the assembled jacket 714 may hold brick 702 snugly in place. In some embodiments, outer magnets 706 and septa 708 may be located inside the jacket to accommodate magnetic connections, which are similar to the magnetic connections, which are part of any module that does not include a jacket. The module with the jacket creates strengthened module 710.

The configuration of connection between the jacket and the microfluidic module illustrated in FIG. 7B comprises a PDMS brick 702 placed in a mold 704 and liquid PDMS containing iron particles may be poured around the brick, creating a border. The PDMS is placed in the mold 704 prior to connecting it with the jacket pieces 724. The PDMS may be cured (i.e., solidified) to afford cured PDMS 720 and then individual jacket pieces 724 may magnetically snap together with the magnetized brick. The jacket pieces may contain inner magnets thus allowing them to snap together with other jacket pieces, which also comprise inner magnets. Once the jacket pieces 724 are connected around the PDMS brick 702, an assembled strengthened module 730 is created.

According to some embodiments, the jacket pieces may be modular and may thus be connected to one another in different ways such to house microfluidic bricks of various dimensions. The jacket pieces may also easily connect with and disconnect from microfluidic modules.

The configuration of connection between the jacket and the microfluidic module illustrated in FIG. 7C comprises a single complete jacket 740 and a brick 754 may be placed inside jacket 740. The jacket 740 may have attached thereon outer magnets 742 and septa 744, such as to create a complete jacket 750. Subsequently, sufficient uncured liquid PDMS 752 is poured over brick 754 such that the total volume of the brick with the uncured PDMS matches the volume inside the complete jacket 750. The liquid PDMS 752 may be cured, i.e., solidified and brick 754 may be securely held in place in substantially the center of jacket 750. Thus, jacket 750 may be connected and attached to brick 754 using physical, magnetic, and/or chemical means. Once the brick 754 is secured within jacket 750 following the addition of liquid PDMS 752, an assembled strengthened module 760 is created.

According to some embodiments, the single piece jacket construction may be sturdier compared to a jacket that is comprised of a plurality of smaller pieces. The single piece jacket may be connected to a brick (in the case of a PDMS microfluidic brick) by adding more PDMS and creating a permanent bond of the device to the jacket for a sturdier connection.

According to some embodiments, the jacket, whether comprising a single compete piece or comprising a plurality of pieces, which are required to snap together to form the housing around a microfluidic module, may be made from polymethylmethacrylate (PMMA), polystyrene, polycarbonate, 3D printed resin (proprietary), thermoplastics such as Acrylonitrile Butadiene Styrene (ABS) or Polylactic Acid (PLA), and/or glass or any combination thereof. The jacket may comprise circuitry contained within, which may comprise conductive wiring and common electrical components (e.g., resistors, capacitors, microcontrollers, sensors, etc.). Just circuitry may be used to transfer power and information throughout the system and from one microfluidic module to another.

According to some embodiments, the outer magnets may be made from Neodymium or any other strong magnetic material. The size and shape of the outer magnets may be of any kind.

According to some embodiments, the septa, which may be attached to a jacket, may be used for maintaining leak-proof connections between adjacent modules, and may help in maintaining sterility within the fluidic circuit comprised of a plurality of modules connected to one another. The size and shape of the septa may be flat, or cylindrical of varying thicknesses. According to some embodiments, the septa may be made of Chlorobutyl, Ethylene tetrafluoroethylene (ETFE), Natural Rubber, Polytetrafluoroethylene (PTFE)/Butadiene, Silicone or any combination thereof.

According to some embodiments, using the unique in-plane PDMS device with magnetic connections along with the jacket system allows for existing PDMS devices and designs to be retrofitted, such that no fundamental design changes are necessary. This is part of enabling a modular system, which makes it easy to select the appropriate microfluidic modules, per required examination, while enabling to change any of the modules in order to change the required system's operation.

According to some embodiments, the jacket may be constructed from a solid and strong material, which may be more resistant to bending, deformation, and crushing than the material most commonly used to create microfluidic devices, i.e., PDMS. Thus, the microfluidic module together with the jacket results in a sturdier and more robust module.

In some embodiments, the jacket may be designed to be of a uniform size. Most current microfluidic modules vary in size and shape often due to small inconsistencies in human craftsmanship or due to quality control issues. The jacket is thus designed with standard dimensions larger than the device itself and can add the necessary addition to width, height, length that a module requires to be brought to a standard size.

In addition, the jacket, being fabricated from a hard material may be more amenable to integration with circuitry and other electronic components, for example, a wirelessly controlled solenoid-actuated micro-valve. Furthermore, the hard jacket material may be more suitable to integration with magnets, which are used for creating connections between modules, such that the magnets will not move or wear as easily as when integrated within a soft material.

Reference is now made to FIGS. 8A-8C, which schematically illustrate connections between a modular microfluidic module and a jacket, according to embodiments of the disclosure. FIG. 8A illustrates the components that would create an assembled strengthened module, according to the second configuration illustrated in FIG. 7B, in more detail. According to the second jacket assembly configuration, the jacket may be comprised of a plurality of pieces 804, each of the pieces including inner magnets 806 to enable the jacket pieces to snap and thus connect to one another. In other embodiments, other means for connecting the jacket pieces together may be implemented. The jacket pieces are to cover and house a brick 802. Typically, each of the jacket pieces 804 may comprise at least one outer magnet 808. The outer magnets 808 are magnetic connectors that allow different modules to be connected to one another. In some embodiments, the outer magnet 808 may have attached thereon, between the outer magnet 808 and a jacket piece, a septum or septa 810. As mentioned hereinabove, the septa may be used for maintaining leak-proof connections between adjacent modules, and may help in maintaining sterility within the fluidic circuit comprised of a plurality of modules connected to one another. In some embodiments, the connection between adjacent microfluidic modules, each housed within a jacket, may be made via a needle adaptor, e.g., needle adaptor 812. As illustrated in FIG. 8B, needle adaptor 812 may comprise a needle inserted through a flexible element. One side of the needle may be configured to be inserted onto a first microfluidic module, while the opposite side of the need 812 may be configured to be inserted into a second adjacent microfluidic module, as illustrated in FIG. 8C. In some embodiments, the needle adapter 812 may be composed of a ferrite stainless steel, which may provide attraction to and alignment with the outer magnetic connectors of the different microfluidic modules.

Reference is now made to FIGS. 9A-9G, which are schematic illustrations of jackets comprised of different numbers of pieces, according to embodiments of the disclosure. According to some embodiments, there may be different configurations of a jacket configured to house a microfluidic module, and provide the microfluidic module with robust sturdiness and protection. A jacket may be designed to fit around the brick and depending on the size and shape of the brick, the jacket may be configured in several ways. FIGS. 9A-9G illustrate some of the configurations that may be used to create a jacket, including a single piece jacket, two configurations of two-piece jackets, two configurations of four-piece jackets, a six-piece jacket and an eight-piece jacket. The jackets may be designed to maintain the planar connections of the bricks and also rely on magnetic, physical or a combination of the two in order to connect the pieces of a jacket and to connect two different jackets to one another.

The single piece jacket of FIG. 9A conforms to the configuration detailed hereinabove with respect to FIG. 7C. the two-piece jacket may have two configurations; one includes the connection between the two pieces located along the transverse axis of the microfluidic module (FIG. 9B), while the other includes the connection between the two pieces located along the longitudinal axis of the microfluidic module (FIG. 9C).

The four-piece jacket may also comprise two configurations, one includes the connection between each three pieces being located along the transverse axis of the microfluidic module (FIG. 9D), while the other includes the connection between each three pieces being located along the longitudinal axis of the microfluidic module (FIG. 9E).

The six-piece jacket may comprise connections located along the longitudinal and transverse axes of the microfluidic module (FIG. 9F), similarly to the eight-piece jacket (FIG. 9G).

Figure 10A:
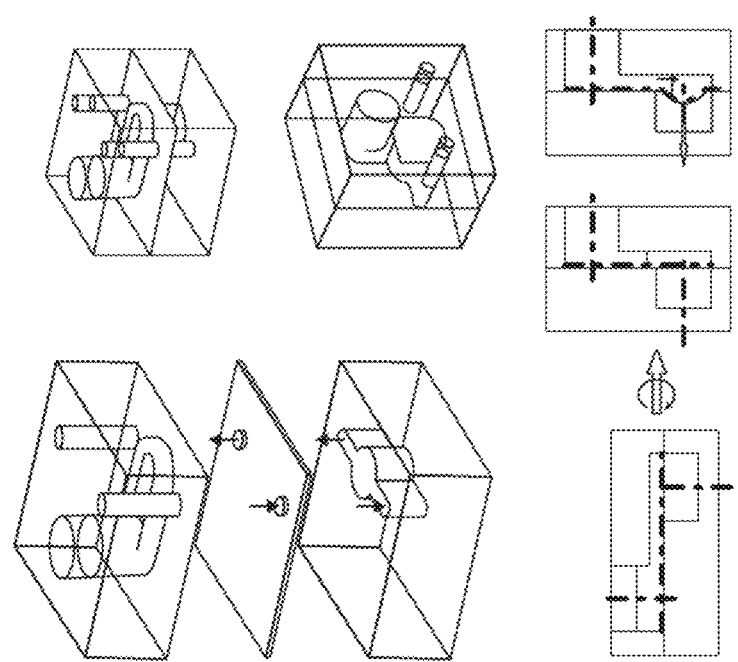
FIGS. 10A-10C are schematic illustrations of an exploded diagram of a prior art lung-on-a-chip device, the actual lung-on-a-chip device, and a planar modular microfluidic system that is equivalent to the lung-on-a-chip device, respectively, according to embodiments of the disclosure.
Figure 10B:
Figure 10C:
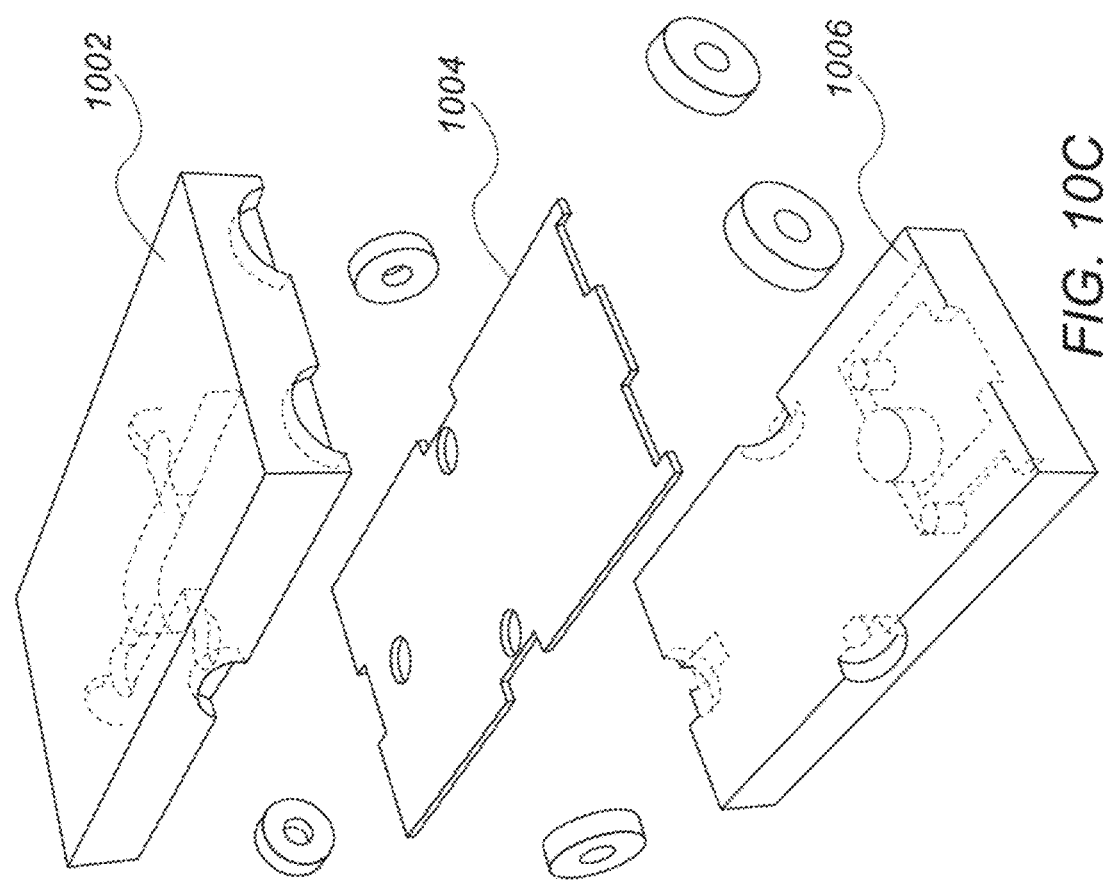

Reference is now made to FIGS. 10A-10C, which are schematic illustrations of an exploded diagram of a prior art lung-on-a-chip device, the actual lung-on-a-chip device, and a planar modular microfluidic system that is equivalent to the lung-on-a-chip device, respectively, according to embodiments of the disclosure. FIGS. 10A-B illustrate a prior art lung-on-a-chip device, while FIG. 10C illustrates a planar modular microfluidic system that performs the same operation but has the advantages of being planar, by including lateral connection instead of top-oriented connection between modules, and of being modular by comprising modular microfluidic units that enable change of orientation, or even change of a module with a different one.

FIG. 10A illustrates an exploded diagram of a lung-on-a-chip device created by Takayama Lab (Lab on a Chip 11(4):609-19 Feb. 2011). The Takayama Lab device is composed of several layers; a cell culture chamber layer and an actuation chamber layer, where an air vacuum chamber may be used to mimic the stress associated with cells lining the alveoli of the human lung in cases of illness. The actual Takayama Lab device used and illustrated in FIG. 10B, was comprised of PDMS and did not conform to any standard dimensions. However, a corresponding and equivalent modular microfluidic system that may be created to perform exactly the same function as the Takayama Lab lung-on-a-chip device is illustrated in FIG. 10C. This planar modular microfluidic system comprises a tissue culture chamber 1002, a semi-permeable membrane 1004 and an actuation chamber 1006, which perform the same function as the prior art lung-on-a-chip. Cells may be introduced into the tissue culture chamber 1002 and allowed to be attached onto membrane 1004. The tissue culture chamber 1002 may then be filled with liquid suitable for growing the cells. The actuation chamber 1006 may be connected to vacuum, which would deform membrane 1004, and thereby deform the lung epithelium attached on membrane 1004. It should be noted that although the orientation of chambers 1002 and 1006 is top-oriented, the connection ports are all located at the lateral surface of the module, as opposed to the prior art which includes top-oriented connections. Thus, the planar modular microfluidic module of the present disclosure, and of the present example, may enable lateral connections between such an exemplary module and other planar modular microfluidic modules. This planar modular microfluidic system comprises of lateral (instead of top-oriented) connections between the different modules. The planar modular microfluidic system conforms with defined standardized dimensions and integrates magnetic connectors for connecting between modular microfluidic modules. That is, the planar modular microfluidic system provided in the present disclosure makes it is possible to convert top-oriented microfluidic systems into planar modular microfluidic system, which enable modularity, imaging under HCS systems (e.g., Perkin Elmer Operetta imaging system). Other prior art microfluidic systems may also be converted into planar modular microfluidic systems, while providing the same function and with the advantages of modularity, ease of assembly, conformity with standardized dimensions, lateral connections, etc.

Figure 11:
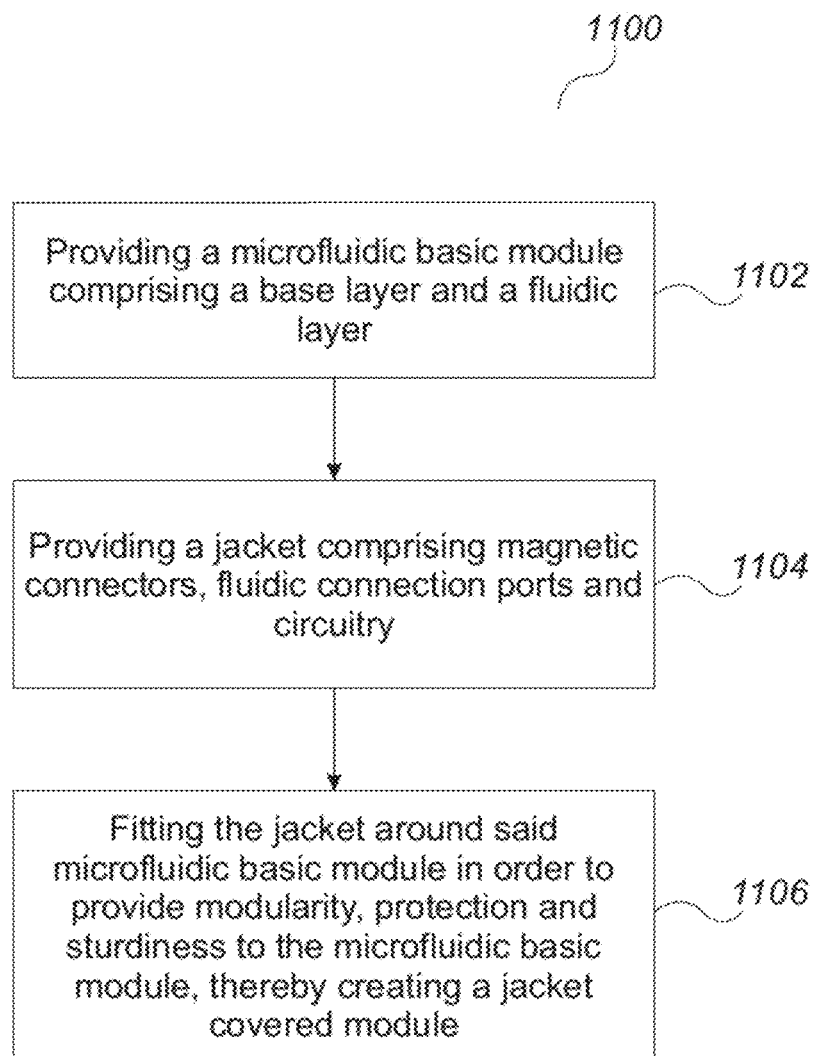
FIG. 11 is a schematic flowchart illustrating a method for manufacturing a microfluidic module, according to embodiments of the disclosure.

Reference is now made to FIG. 11, which is a schematic flowchart illustrating a method for manufacturing a microfluidic module, according to embodiments of the disclosure. According to some embodiments, a method 1100 for manufacturing planar modular microfluidic modules may comprise operation 1102, which comprises providing a basic microfluidic module comprising a base layer, and a fluidic layer. In some embodiments, the microfluidic module may further comprise a top layer, and a plug. As illustrated in FIG. 1A, each planar modular microfluidic module or brick comprises a base layer onto which a fluidic layer is positioned, which includes the fluidic channels. In some embodiments on top of the fluidic layer may be a top layer. In some embodiments, the top layer, fluidic layer and base layer may be made of PDMS, though other materials may be used.

Each planar modular microfluidic module may further comprise at least one plug or stopper, typically positioned on opposite sides of the planar modular microfluidic module.

According to some embodiments, method 1100 may further comprise operation 1104, which may comprise providing a jacket comprising magnetic connectors, fluidic connection ports and circuitry. As detailed hereinabove with respect to FIG. 8A, a jacket that is configured to house the planar modular microfluidic module may comprise outer magnets acting as magnetic connectors (e.g., magnetic connectors 808, FIG. 8A) between adjacent planar modular microfluidic modules. In addition, a jacket may comprise fluidic connection ports (e.g., fluidic port 814, FIG. 8A), which may be located within the magnetic connectors. Furthermore, a jacket may comprise circuitry within in order to enable power transfer from, for example, a battery pack module (e.g., module 510, FIGS. 5A-5B) to any planar modular microfluidic module that is in need for energy for its proper operation.

According to some embodiments, method 1100 may further comprise operation 1106, which comprises fitting the jacket around the basic microfluidic module in order to provide modularity, protection and sturdiness to the microfluidic module, thereby creating a jacket covered module. As detailed above with respect to FIGS. 7A-7C, the jacket may provide additional protection and sturdiness to the less strong material that the planar modular microfluidic module is made of. In addition, the jacket provides modularity since it adjusts the size of the planar modular microfluidic module to a standardized dimension, such enabling using modules interchangeably, replacing one with another, and being able to connect any module to any other module in an easy and quick manner. Conjugated terms such as, by way of example, 'a thing property' implies a property of the thing, unless otherwise clearly evident from the context thereof. In case electrical or electronic equipment is disclosed it is assumed that an appropriate power supply is used for the operation thereof.

The flowchart and block diagrams illustrate architecture, functionality or an operation of possible implementations of systems and methods according to various embodiments of the present disclosed subject matter. It should also be noted that, in some alternative implementations, illustrated or described operations may occur in a different order or in combination or as concurrent operations instead of sequential operations to achieve the same or equivalent effect.

The corresponding structures, materials, acts, and equivalents of all means or step plus function elements in the claims below are intended to include any structure, material, or act for performing the function in combination with other claimed elements as specifically claimed. As used herein, the singular forms "a", "an" and "the" are intended to include the plural forms as well, unless the context clearly indicates otherwise. It will be further understood that the terms "comprising", "including" and/or "having" and other conjugations of these terms, when used in this specification, specify the presence of stated features, integers, steps, operations, elements, and/or components, but do not preclude the presence or addition of one or more other features, integers, steps, operations, elements, components, and/or groups thereof.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions and equivalents are not precluded.

The invention claimed is:

1. A planar modular microfluidic module comprising:
 a base layer;
 a fluidic layer, configured to be attached to and on top of the base layer;
 a physical connector configured to enable lateral connection between adjacent modules, said physical connector positioned on at least one lateral side of said planar modular microfluidic module, wherein said physical connector is open parallel to major fluid flow axis; and
 a fluidic connection port configured to enable fluid flow connection between adjacent modules, wherein said fluidic connection port is located within said physical connector.

2. The planar modular microfluidic module according to claim 1, further comprising conduction nodes configured to provide integrated circuitry for electrical connection or data transfer between adjacent modules.

3. The planar modular microfluidic module according to claim 1, wherein said base layer comprises circuitry or electronic components.

4. The planar modular microfluidic module according to claim 1, wherein said fluidic layer comprises fluidic channels for fluid flow between adjacent modules.

5. The planar modular microfluidic module according to claim 4, wherein said planar modular microfluidic module comprises more than one fluidic connection port arranged in a diagonal manner within at least one physical connector such to enable an imaging system to image the fluidic channels.

6. The planar modular microfluidic module according to claim 1, further comprising a top layer configured to be bonded to the fluidic layer, such to conform the planar modular microfluidic module to a standardized size.

7. The planar modular microfluidic module according to claim 1, further comprising a plug located on the at least one lateral side of said planar modular microfluidic module, said plug configured to prevent flow there through.

8. The planar modular microfluidic module according to claim 1, wherein said planar modular microfluidic module comprises more than one physical connector located on the at least one lateral side of said planar modular microfluidic module and arranged in a diagonal orientation relative to the fluidic layer.

9. The planar modular microfluidic module according to claim 1, wherein said physical connector is a magnetic connector.

10. The planar modular microfluidic module according to claim 1, wherein said fluidic layer is made of Polydimethylsiloxane (PDMS), polymethylmethacrylate (PMMA), Polyethylene terephthalate (PET), polystyrene, polycarbonate, clear 3D printed resin, glass, or any combination thereof.

11. The planar modular microfluidic module according to claim 1, wherein said base layer is made of Polydimethylsiloxane (PDMS), polymethylmethacrylate (PMMA), Polyethylene terephthalate (PET), polystyrene, polycarbonate, clear 3D printed resin, glass, or any combination thereof, with addition of neodymium or any other strong magnet.

12. The planar modular microfluidic module according to claim 1, wherein said planar modular microfluidic module is configured to be imaged by a fluorescence microscope, a confocal microscope, or high content screening (HCS) imaging systems.

13. The planar modular microfluidic module according to claim 1, wherein said planar modular microfluidic module is configured to connect to any type of fluidic connector.

14. The planar modular microfluidic module according to claim 13, wherein the fluidic connector is selected from a group consisting of: a four-way connector configured to enable fluid flow through four outlets, a three-way connector configured to enable fluid flow through three outlets, a two-way 'L' shaped connector configured to enable fluid flow through two outlets positioned perpendicularly to one another, and a two-way straight connector configured to enable fluid flow through two outlets positioned along one line.

15. A planar modular microfluidic module, said planar modular microfluidic module comprising:
 a base layer; and
 a fluidic layer, said fluidic layer configured to be attached to and on top of the base layer; said base layer and said fluidic layer configured to create a single base module;
 a jacket configured to cover said single base module around its lateral sides, in order to provide sturdiness to said single base module and create a jacket covered module, wherein said jacket comprises:
 a physical connector configured to enable lateral connection between adjacent jacket covered modules, said physical connector positioned on at least one lateral side of said jacket covered module, wherein said physical connector is open parallel to major fluid flow axis;
 a fluidic connection port configured to enable fluid flow connection between adjacent jacket covered modules, wherein said fluidic connection port is located within said physical connector; and
 a plurality of jacket pieces connected to one another around said single base module via inner magnetic connectors located within each of the plurality of jacket pieces.

16. The planar modular microfluidic module according to claim 15, wherein said physical connector is a magnetic connector.

17. The planar modular microfluidic module according to claim 15, wherein said jacket comprises septa positioned between said jacket and said physical connector, said septa configured to maintain leak-proof connections between adjacent jacket covered modules.

18. The planar modular microfluidic module according to claim 15, wherein said jacket comprises a needle adaptor configured to enable fluidic connection between adjacent jacket covered modules.

19. The planar modular microfluidic module according to claim 15, wherein said jacket is configured to house the single base module with addition of solidified liquid PDMS positioned in between said single base module and said jacket.

20. The planar modular microfluidic module according to claim 15, wherein said jacket further comprises circuitry configured to provide electrical connection between adjacent jacket covered modules.

21. The planar modular microfluidic module according to claim 15, wherein said planar modular microfluidic module is capable of performing a biological or an engineering function.

22. The planar modular microfluidic module according to claim 15, wherein a plurality of planar modular microfluidic modules is connected to one another, further wherein the order and type of said plurality of planar modular microfluidic modules is interchangeable.

23. The planar modular microfluidic module according to claim 15, wherein said planar modular microfluidic module is configured to be imaged by a fluorescence microscope, a confocal microscope, or high content screening (HCS) imaging systems.

24. The planar modular microfluidic module according to claim 15, wherein said jacket covered module comprises at least two physical connectors located on at least one lateral side of said jacket covered module and arranged in a diagonal manner relative to a lateral side of the planar modular microfluidic module.

25. The planar modular microfluidic module according to claim 24, wherein said jacket covered module comprises at least two fluidic connection ports arranged in a diagonal manner within the at least two physical connectors such to enable an imaging system to image fluidic channels connected by the at least two fluidic connection ports.

26. Within a planar modular microfluidic module, an at least one microfluidic connector comprising:
 an at least one physical connector configured to enable lateral connection between adjacent planar microfluidic modules, said physical connector positioned on at least one lateral side of the planar modular microfluidic module, wherein said physical connector is open parallel to major fluid flow axis; and
 an at least one fluidic connection port configured to enable fluid flow connection between adjacent planar microfluidic modules, wherein said at least one fluidic connection port is located within said at least one physical connector.

27. The microfluidic connector according to claim 26, further comprises at least one conducting node for conducting an electrical charge or data.

28. A method for manufacturing a planar modular microfluidic module, said method comprising:
 providing a microfluidic base module comprising a base layer, and a fluidic layer;
 providing a plurality of jacket pieces, said plurality of jacket pieces comprising magnetic connectors, fluidic connections ports, and circuitry, wherein said plurality of jacket pieces are connected to one another around said base module;
 assembling the plurality of jacket pieces via inner magnetic connectors located within each of the plurality of jacket pieces to form a jacket, said magnetic connectors positioned on at least one lateral side of said jacket, wherein said magnetic connectors are open parallel to major fluid flow axis, wherein said fluidic connection ports are located within said magnetic connectors; and
 fitting the jacket around said microfluidic base module in order to provide modularity, protection and sturdiness to the microfluidic base module, thereby creating a jacket covered module.

29. The planar modular microfluidic module according to claim 1, wherein said fluid flow connection between adjacent modules is not top-oriented.

* * * * *